(12) United States Patent
Fenard et al.

(10) Patent No.: US 10,596,264 B2
(45) Date of Patent: Mar. 24, 2020

(54) PEPTIDES WITH VIRAL INFECTION ENHANCING PROPERTIES AND THEIR USE

(75) Inventors: David Fenard, Mennecy (FR); Antoine Kichler, Traemheim (FR); Samia Martin, Savigny sur Orge (FR)

(73) Assignees: Genethon, Evry (FR); Centre National de la Recherche Scientique, Paris (FR); Institut National de la Sainte et de la Recherche Madicale, Paris (FR)

( * ) Notice: Subject to any disclaimer, the term of this patent is extended or adjusted under 35 U.S.C. 154(b) by 417 days.

(21) Appl. No.: 14/130,285

(22) PCT Filed: Jun. 28, 2012

(86) PCT No.: PCT/EP2012/062642
§ 371 (c)(1),
(2), (4) Date: May 20, 2014

(87) PCT Pub. No.: WO2013/001041
PCT Pub. Date: Jan. 3, 2013

(65) Prior Publication Data
US 2014/0255349 A1  Sep. 11, 2014

(30) Foreign Application Priority Data
Jun. 30, 2011  (EP) .................................... 11172279

(51) Int. Cl.
*A61K 38/00* (2006.01)
*A61K 38/16* (2006.01)
*C07K 14/00* (2006.01)
*C12N 15/63* (2006.01)
*A61K 47/42* (2017.01)
(Continued)

(52) U.S. Cl.
CPC ............ *A61K 47/42* (2013.01); *C07K 14/001* (2013.01); *C07K 14/47* (2013.01); *C12N 15/86* (2013.01); *A61K 38/00* (2013.01); *C12N 2740/10043* (2013.01)

(58) Field of Classification Search
CPC ...... C07K 14/001; C07K 14/47; C07K 14/00; A61K 47/42; A61K 38/00; A61K 38/16; C12N 15/86; C12N 15/63; C12N 2740/10043
See application file for complete search history.

(56) References Cited

U.S. PATENT DOCUMENTS

| 7,759,467 B2 | 7/2010 | Williams et al. |
| 2003/0045465 A1* | 3/2003 | Mixson ................ A61K 9/1272 514/1.2 |

(Continued)

FOREIGN PATENT DOCUMENTS

| WO | 1992/013882 A1 | 8/1992 |
| WO | 2002/096928 A2 | 12/2002 |

(Continued)

OTHER PUBLICATIONS

Kichler et al 2006, Biochimica et Biophysica Acta 1758: 301-307.*
(Continued)

*Primary Examiner* — Kevin K Hill
(74) *Attorney, Agent, or Firm* — Fox Rothschild LLP

(57) ABSTRACT

The invention relates to LAH4 peptides and functional derivatives thereof and their use for improving transduction efficiency of viruses into target cells.

Figure 1:
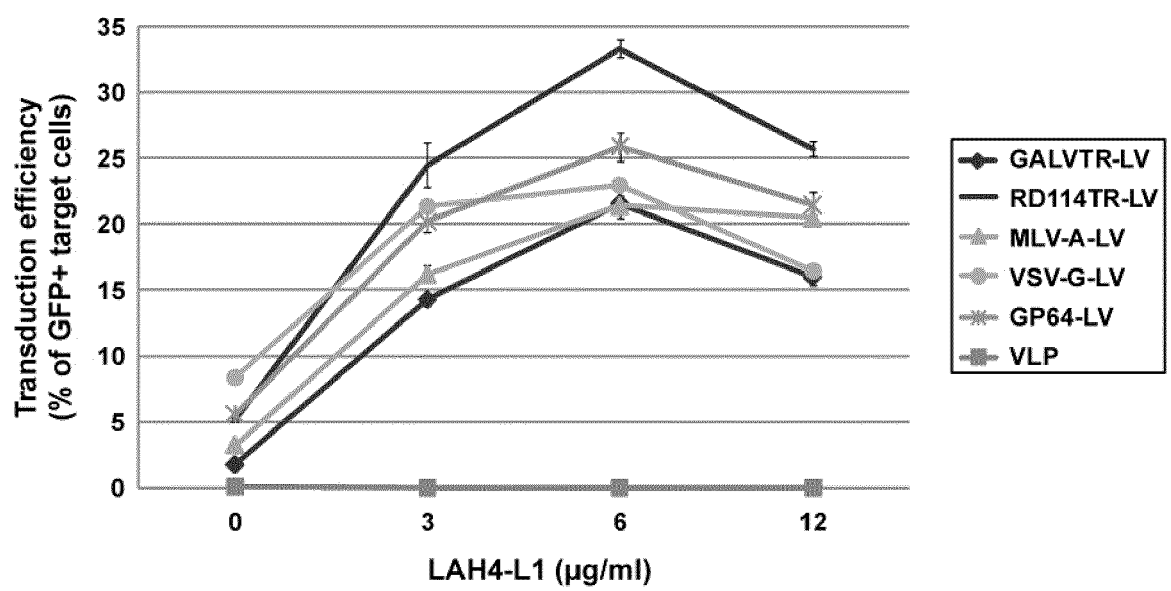
Figure 1:
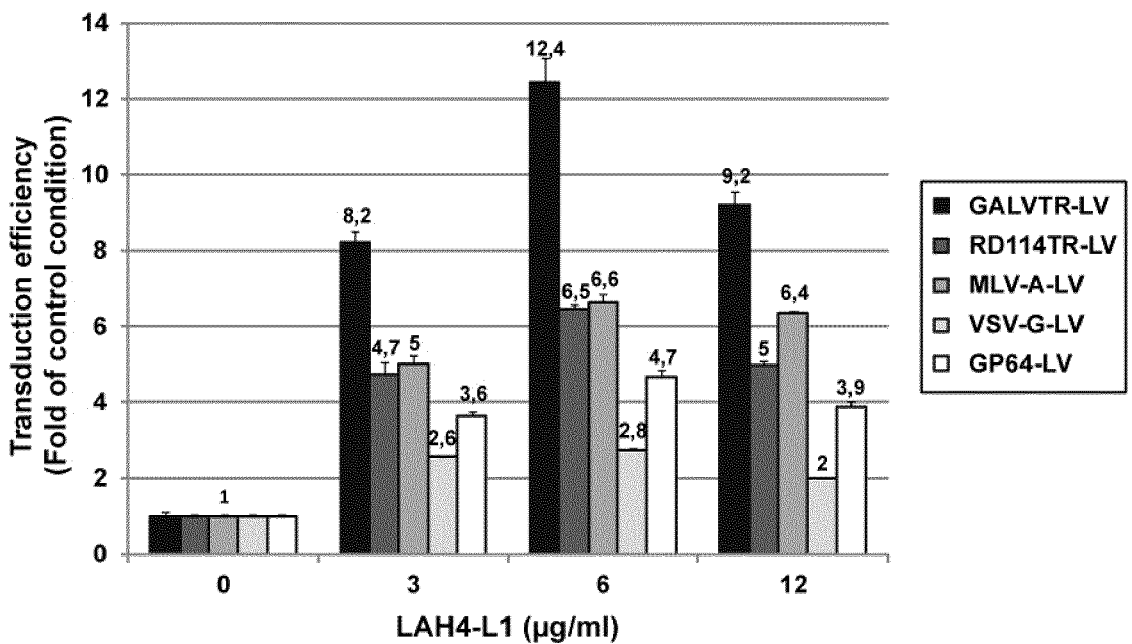

15 Claims, 12 Drawing Sheets
Specification includes a Sequence Listing.

(51) Int. Cl.
C12N 15/86 (2006.01)
C07K 14/47 (2006.01)

(56) References Cited

U.S. PATENT DOCUMENTS

| | | | | |
|---|---|---|---|---|
| 2003/0219826 | A1* | 11/2003 | Robbins | A61K 47/48238 435/7.1 |
| 2005/0003546 | A1* | 1/2005 | Sessa | A61K 48/0008 435/456 |
| 2008/0287342 | A1* | 11/2008 | Yu | A61K 38/10 514/1.1 |
| 2018/0318447 | A1* | 11/2018 | Majdoul | A61K 48/0016 |

FOREIGN PATENT DOCUMENTS

| | | | |
|---|---|---|---|
| WO | WO 02/096928 | * | 12/2002 |
| WO | 2007/085630 A1 | | 8/2007 |
| WO | WO 02/096928 | * | 2/2009 |

OTHER PUBLICATIONS

Eto et al, Peptides 30: 1548-1552, 2009.*
Mann et al, Drug Discovery Today 13(3/4): 152-160, 2008.*
Kabouridis, TRENDS in Biotechnol. 21(11): 498-503, 2003.*
Kichler et al, Biochimica et Biophysica Acta 1758: 301-307, 2006.*
Varkouhi et al, J. Controlled Release 151:220-228, 2011; available online Nov. 13, 2010.*
Mann et al, Drug Discovery Today 13(3/4): 152-160, 2007.*
Vermeer et al, Acta Biomaterialia 64: 259-268, 2017.*
International Search Report dated Sep. 19, 2012, in Application No. PCT/EP2012/062642.
International Preliminary Report on Patentability dated Jan. 7, 2014, in Application No. PCT/EP2012/062642.
Bechinger, "Towards membrane protein design: pH-sensitive topology of histidine-containing polypeptides" J. Mol Biol, 1996, vol. 263, pp. 768-775.
Charrier et al., "Quantification of lentiviral vector copy numbers in individual hematopoietic colony-forming cells shows vector dose-dependent effects on the frequency and level of transduction," Gene Ther, 2011, vol. 18, pp. 479-487.
Davis et al., "Charged polymers modulate retrovirus transduction via membrane charge neutralization and virus aggregation," Biophys, 2004, vol. 86, pp. 1234-1242.
D'Costa et al., "Lentiviral vectors in clinical trials: Current status," Curr Opin Mol Ther, 2009, vol. 11, pp. 554-564.
Fenard D et al: "Vectofusin-1 Augments Lentiviral Transduction of Human Hematopoietic Cells by Enhancing Adhesion and Fusion of Particles to CD34+Cells." Molecular Therapy 20(Supp. 1): S90. (2012).
Follenzi et al., "Gene transfer by lentiviral vectors is limited by nuclear translocation and rescued by HIV-1 pol sequences," Nat. Genet, 2000, vol. 25, pp. 217-222 (Abstract only).
Georgescu et al., "NMR structures of the histidine-rich 5 peptide LAH4 in micellar environments: Membrane insertion, pH-dependent mode of antimicrobial action, and DNA transfection," Biophys. J., 2010, vol. 99, pp. 2507-2515.
Jacome et al., "Lentiviral-mediated genetic correction of hematopoietic and mesenchymal progenitor cells from Fanconi anemia patients," Mol Ther, 2009, vol. 17, pp. 1083-1092.
Kichler et al., "Histidine-rich amphipathic peptide antibiotics promote efficient delivery of DNA into mammalian cells," Proc Natl Acad Sci USA, 2003, vol. 100, pp. 1564-1568.
Kutner et al., "Production, concentration and titration of pseudotyped HIV-1-based lentiviral vectors," Nat Protoc, 2009, vol. 4, pp. 495-505 (Abstract only).
Kyte et al., "A simple method for displaying the hydropathic character of a protein," J. Mol. Biol, 1982, vol. 157, pp. 105-132.
Langlet-Bertin Bet al: "Design and Evaluation of Histidine-Rich Amphipathic Peptides for siRNA Delivery." Pharmaceutical Research 27(7): 1426-1436. (2010) (Abstract only).
Legrand et al., "Experimental model for the study of the human immune system: production and monitoring of 'Human Immune System' Rag2-/-gamma C-/•mice," Methods Mol. Biol., 2008, vol. 415, pp. 65-82 (Abstract only).
Mason et al., "Structural determinants of antimicrobial and antiplasmodial activity and selectivity in histidine-rich amphipathic cationic peptides," J Biol Chem, 2009, vol. 284, pp. 119-133.
Merten et al., "Large-scale manufacture and characterization of a lentiviral vector produced for clinical ex vivo gene therapy application," Hum Gene Ther, 2011, vol. 22, pp. 343-356 (Abstract only).
Merten, O.W., "State-of-the-art of the production of retroviral vectors" J. Gene Med, 2004, vol. 6., Suppl 1, pp. S105-S124 (Abstract only).
Munch et al., "Semen-derived amyloid fibrils drastically enhance HIV infection," Cell, 2007, vol. 131, pp. 1059-1071.
Naldini et al., "In vivo gene delivery and stable transduction of nondividing cells by a lentiviral vector," Science, 1996, vol. 272, pp. 263-267 (Abstract only).
Novelli et al., "Ex vivo culture of cord blood CD34+ cells expands progenitor cell numbers, preserves engraftment capacity in nonobese diabetic/severe combined immunodeficient mice, and enhances retroviral transduction efficiency," Hum Gene Ther, 1999, vol. 10, pp. 2927-2940 (Abstract only).
Pollok et al., "Facilitation of retrovirus-mediated gene transfer into hematopoietic stem and progenitor cells and peripheral blood T-lymphocytes utilizing recombinant fibronectin fragments," Curr Opin Mol Ther, 1999, vol. 1, pp. 595-604 (Abstract only).
Roan et al, "The cationic properties of SEVI underlie its ability to enhance human immunodeficiency virus infection," J Virol, 2009, vol. 83, pp. 73-80.
Rodrigues et al., "Purification of retroviral vectors for clinical application: biological implications and technological challenges," J Biotechnol, 2007, vol. 127, pp. 520-541 (Abstract only).
Sandrin et al., "Lentiviral vectors pseudotyped with a modified RD114 envelope glycoprotein show increased stability in sera and augmented transduction of primary lymphocytes and CD34+ cells derived from human and nonhuman primates," Blood, 2002, vol. 100 pp. 823-832 (Abstract only).
Schiffer et al., "Use of helical wheels to represent the structures of proteins and to identify segments with helical potential," Biophys. J, 1967, vol. 7, pp. 121-135.
Wurm et al., "The influence of semen-derived enhancer of virus infection on the efficiency of retroviral gene transfer," J Gen Med, 2010, vol. 12 pp. 137-146 (Abstract only).

* cited by examiner

A

B

A

B

C

A

B

C

A

B

C

PEPTIDES WITH VIRAL INFECTION ENHANCING PROPERTIES AND THEIR USE

CROSS REFERENCE TO RELATED APPLICATIONS

The present application is the U.S. National Phase of International Patent Application Ser. No. PCT/EP12/62642, filed Jun. 28, 2012, which claims priority to European Patent Application. Ser. No. 11172279.9, filed Jun. 30, 2011, both of which are hereby incorporated by reference in their entireties.

The invention relates to peptides and functional derivatives thereof and their use for improving transduction efficiency of viruses into target cells.

BACKGROUND OF THE INVENTION

Gene therapy approaches are often hampered by low transduction efficiencies of target cells by recombinant viral vectors. Retroviral vectors, and in particular human immunodeficiency virus 1 (HIV-1)-based lentiviral vectors (LVs) are promising vehicles for gene therapy (D'Costa et al., 2009). These vectors are used currently in clinical applications to treat various diseases such as immune deficiencies, neurodegenerative or neurological diseases, anemias, HIV infection. Some of the applications of retroviral vectors rely on the transduction of specific target cells ex vivo such as hematopoietic stem/progenitor cells expressing the CD34 marker. A limiting factor with the use of recombinant lentiviral particles, is the capacity to obtain highly infectious titers during production of recombinant lentiviral vector particles. One way to circumvent this limitation is to concentrate the viral supernatant during the purification steps (Rodrigues et al., 2007). However, purification protocols are difficult to establish for some LVs, depending on the envelope glycoproteins used to pseudotype viral particles as it is the case for GALVTR-LVs (LVs pseudotyped with gibbon ape leukemia virus envelope glycoprotein fused to the cytoplasmic tail of the amphotropic murine leukemia virus (MLV-A) envelope glycoprotein (Sandrin et al., 2002)). Therefore, many lentiviral vector preparations have low titer and transduction efficacy is limited. Another limiting factor is the ability of the lentiviral vector itself to infect target cells. Several envelope glycoproteins such as VSV-G, RD114TR, GALVTR can be used to pseudotype lentiviral vectors and have variable infectivity on target cells such as CD34+ cells (Sandrin et al., 2002). One strategy to circumvent these limitations is the addition of cofactors to optimize transduction protocols like cationic polymers (e.g. polybrene) or fibronectin fragments (e.g. retronectin) (Davis et al., 2004; Pollok et al., 1999). U.S. Pat. No. 7,759,467 describes a method for increasing the efficiency of transduction of hematopoietic cells by retroviruses comprising the infection of the cells in the presence of fibronectin or fibronectin fragments. However, the proposed method is not totally satisfactory for at least two reasons. First, the fragments of fibronectin used for improving the efficiency of retroviruses present significant economic drawbacks since they usually comprise around 270 or more amino acids. Furthermore, the use of fibronectin or fibronectin fragments requires coating of the culture plates and preloading of viral supernatants onto immobilized fibronectin fragments. These two steps are difficult to standardize and can lead to some saturation of target cell transduction depending on the concentrations of fibronectin fragments and viral supernatants used (Novelli et al., 1999).

Interestingly, natural cationic peptides called SEVI have been recently identified in human semen as strong enhancers of HIV-1 infectivity (Munch et al., 2007; Roan et al., 2009). This family of peptides has also been disclosed in international application No. PCT/EP2007/050727, which describes fragments of amino acid residues 240-290 of human prostatic acid phosphatase which promote viral infection of a cell.

International application No. PCT/FR02/01772 describes amphipathic cationic peptides having an absolute charge higher than or equal to 2 at pH 7.4 and comprising at least one hydrophilic portion, said portion comprising at least three residues which are capable of being protonized at a pH of less than 7.4 in order to transfer a nucleic acid or a protein in a cell. This document does not describe or suggest the use of such peptides for improving the transduction efficiency of a virus or viral vector. Furthermore, these amphipathic cationic peptides harbor antibiotic activities (Mason et al., 2009).

The aim of the inventors was to provide means for improving the transduction efficiency of a virus or viral vector, for example for improving delivery of a gene into target cells. Since peptides are interesting for their biodegradable property, for their reduced size, simplicity of characterization and large-scale production, extensive research has been conducted for identifying alternatives to fibronectin and SEVI peptides.

SUMMARY OF THE INVENTION

The present inventors have found that particular peptides as defined in the claims have the property of promoting the transduction efficiency of viruses in eukaryotic cells and in particular in human primary hematopoietic progenitor/stem cells.

According to one aspect, the invention relates to the use of the LAH4 peptide or a functional derivative thereof for promoting the infection of an eukaryotic cell by a virus or a viral vector.

According to another aspect, the invention relates to a method, in particular an in vitro or ex vivo method, for infecting eukaryotic cells with a virus or a viral vector, comprising contacting the cells with the virus or viral vector in the presence of the LAH4 peptide or a functional derivative thereof.

According to another aspect, the invention relates to a method, in particular an in vivo or ex vivo method, for increasing the efficiency of gene transfer into target cells with viral vectors, comprising contacting the target cells with the viral vector in the presence of the LAH4 peptide or a functional derivative thereof to promote transfer of nucleic acid sequences (such as gene(s), cDNAs, siRNAs, shRNAs, sequences allowing for the production of antisense oligonucleotides) into the target cells.

According to a further aspect, the invention relates to a method for diagnosing an infection by a virus in a subject, comprising incubating a sample of the subject with an eukaryotic cell and the LAH4 peptide or a functional derivative thereof in order to amplify any virus contained in said sample, and identifying the amplified virus.

According to a further aspect, the invention relates to novel LAH4-derived peptides.

According to another aspect, the invention relates to a peptide for use in gene therapy for promoting the infection of an eukaryotic cell by a virus or a viral vector. It further relates to a peptide for use in combination with a virus or viral vector in gene therapy.

DETAILED DESCRIPTION OF THE INVENTION

In the context of the present invention, the term "the LAH4 peptide" refers to the peptide with the amino acid sequence consisting of SEQ ID NO:1.

As used herein, the term "LAH4 functional derivative" and declinations thereof means any peptide whose sequence has been designed based on the primary structure of the LAH4 peptide and having the ability to improve the transduction efficiency of a virus or viral vector. In particular embodiment, a LAH4 functional derivative is a peptide having the ability to improve the transduction efficiency of a virus encapsidated with a GALV, RD114, MLV, VSV or GP64 envelope in eukaryotic cells, in particular human, mouse, rat, monkey, dog or hamster cells, in particular a human CD34+ cell. In a specific embodiment, the LAH4 functional derivative is a peptide having the ability to improve the transduction efficiency of a virus encapsidated with a GALV envelope in human CD34+ cells.

A LAH4 functional derivative according to the invention should also comprise the following features:
  it comprises 19 or more amino acids, in particular 20, 21 or more amino acids. In a particular embodiment, the peptide comprises between 20 and 30 amino acids, in particular between 21 and 26, in particular between 24 and 26;
  its N-terminal end comprises one or more amino acid residues positively charged at pH 7.4. In a particular embodiment, the N-terminal end comprises one or two residues positively charged at pH 7.4. In a particular embodiment, these amino acid residues are lysines and/or arginines; and
  its central region forms a helix when represented according to Schiffer-Edmundson's wheel representation (Schiffer et al., 1967) which is well known in the art and correspond to the 18 amino acid residues likely forming the central domain of the peptide. In a particular embodiment, the helix is an α-helix according to Schiffer-Edmundson's wheel representation. In a further embodiment, the peptide according to the invention is a cationic amphipathic peptide or a peptide comprising an apolar helix. According to this embodiment, the central helical region of the peptide is corresponding to the amino acid residues that have a strong propensity to form an helix (Georgescu et al, 2010). In this embodiment, the central helical region of the peptide can be:
  either an apolar helix harboring a cluster of hydrophobic amino acid residues on one side of the helix and consecutive alanine residues on the other side of the helix, said consecutive alanine residues defining an angle of 60 to 180° in Schiffer-Edmundson's wheel representation, and preferentially an angle of 140°;
  or, an amphipathic helix harboring a cluster of hydrophobic amino acid residues on one side of the helix and two to four histidine residues on the other side of the helix, defining an hydrophilic angle comprised between 60° and 180° in Schiffer-Edmundson's wheel representation and preferably an angle of 140°.

In a particular embodiment, the amino acids of the LAH4 functional derivative are selected in the group consisting of alanine, histidine, leucine and lysine.

In the context of the present invention, the term "amphipathic peptide" denotes a peptide comprising hydrophobic and hydrophilic amino acids, which are susceptible of defining at least one hydrophilic region and at least one distinct hydrophobic region, as represented in Schiffer-Edmundson's wheel representation.

In the context of the present invention, the term "apolar helical peptide" denotes a peptide comprising alanine and hydrophobic amino acid residues which are susceptible of defining at least one distinct hydrophobic region, as represented in Schiffer-Edmundson's wheel representation. Representative hydrophobic residues that can be present in the peptides of the invention have an hydropathy index greater or equal to +1.9 (Kyte et al, 1982). Accordingly, representative hydrophobic residues that can be present in the peptides of the invention include valine, isoleucine and leucine. In a preferred embodiment, the hydrophobic residues are leucine residues.

In the context of the present invention, the term "cationic peptide" denotes a peptide which has a positive absolute charge at pH 7.4. In a preferred embodiment, the positive charges are provided by arginine and/or lysine residue(s). Cationic natural amino acids not coded by the genetic code such as ornithine can also provide positive charges in the peptides of the invention.

In an alternative embodiment, positively charged moieties are coupled to amino acid residues. Such positively charged moieties include, for example, ethyleneimine, spermine and spermidine, as is well known in the field.

The LAH4 functional derivative peptides used in the present invention have the property of increasing the transduction efficiency of viruses or viral vectors, and can be selected readily by a person skilled in the art using for instance the methods described in the examples. Described herein are methods for identifying such functional derivatives of the LAH4 peptide. In a particular embodiment, the methods include
  selecting the LAH4 peptide or a known functional derivative thereof (for example one of those mentioned herein below in SEQ ID NOs:1-27), a virus or viral vector of interest and a cell of interest;
  modifying the LAH4 peptide or known functional derivative thereof to prepare a variant peptide; and
  measuring the transduction efficiency of a cell by the virus or viral vector in presence of the variant peptide,
wherein the variant peptide is considered a functional derivative when an efficient transduction is determined.

The methods can also include a step of comparing the transduction efficiency of the virus or viral vector obtained with the variant peptide with the transduction efficiency obtained without the variant peptide, or with the transduction efficiency obtained with a peptide known for its ability to improve the transduction efficiency of the virus or viral vector in the cell.

The step of modifying the LAH4 peptide or a known functional derivative thereof can comprise modifications such as mutation of a first amino acid residue of the LAH4 peptide or known functional derivative thereof to prepare a variant peptide. In a variant embodiment, the modification includes covalently modifying one or more amino acid residues in the LAH4 peptide or a known functional derivative thereof, as provided below. According to another variant, the modification comprises the replacement of the naturally occurring L amino acids by D amino acids (in one or more positions of the peptide, and in particular in all positions).

Exemplary functional derivatives of the LAH4 peptide that can be tested using such methods include the preferred functional derivatives shown in SEQ ID NOs: 2-27. Those same functional derivatives of SEQ ID NOs: 2-27 and the LAH4 peptide of SEQ ID NO:1 can also be used as a basis for the design of further functional derivatives according to the invention. Furthermore, the peptides of SEQ ID NOs: 1-27 that can be used as controls in the methods for identifying functional derivatives according to the invention.

In a particular embodiment of the invention, the peptides comprise amino acid residues selected in the group consisting of alanine, leucine, histidine, arginine and lysine.

In a particular embodiment of the use and methods of the invention, the N-terminal end of the peptide comprises one, two or three positive charge(s). In a specific variant of this embodiment, the positive charge(s) at the N-terminal end of the peptide is (are) provided by arginine or lysine residue(s). In a further variant, the positively charged residues are at the extremity of the N-terminus. In a further variant embodiment, the first amino acid(s) (e.g. the first, or the first and the second residue, or the first and the third, etc.) is(are) neutral residues. In a further embodiment of the use and methods of the invention, the most C-terminal residue is an alanine and in a further aspect, when the C-terminal end of the peptide comprises positively charged amino acid residues at pH7.4, they are located next to the C-terminal alanine or located at the most N-terminal extremity.

Representative residues that can provide positive charges in the C-terminal end are arginine and/or lysine residues.

In a particular embodiment of the use and methods of the invention, the peptide comprises four histidine residues. In a specific embodiment, said histidine residues form two pairs of adjacent histidines in a helix represented according to the Schiffer-Edmundson's wheel. According to a variant of this embodiment, the LAH4 derived peptide comprises only leucine residues or only alanine residues in the portion of the α-helix defined by the smallest angle between the histidine pairs.

According to a specific embodiment, the peptide comprises four histidine residues and is of the sequence $(K/R)_a(K/R)_b(K/A/L)_cL_dL(A/H/L)(A/H/L)(A/L)L(A/H/L)(A/H/L)(A/L)(A/L)(A/L)(H/L)(A/L)$ $(H/L)(A/H/L)(A/L)(A/L)(A/H/L)(A/H/L)_eL_f(K/R)_g(K/R)_hA_i$
wherein:
a, b, c and d represent 0 or 1, with the proviso that a+b+c+d is equal to 2 or 3 or preferably 4; e, f, g, h and i independently represent 0 or 1, with e+f+g+h+i equal to 2 or 3 or 4 or preferably 5.

In a variant embodiment, histidine residues are replaced by other groups which become protonated at acidic pH: these include imidazole containing groups or diaminopropionic acid residues.

Specific peptides used in the invention can be those represented in SEQ ID NO:1 to 27:

| | (SEQ ID NO: 1) |
|---|---|
| LAH4: | KKALLALALHHLAHLALHLALALKKA |

| | (SEQ ID NO: 2) |
|---|---|
| LAH4-L1: | KKALLAHALHLLALLALHLAHALKKA |

| | (SEQ ID NO: 3) |
|---|---|
| LAH4-L1-dKC: | KKALLAHALHLLALLALHLAHALA |

| | (SEQ ID NO: 4) |
|---|---|
| LAH4-L1-R: | RRALLAHALHLLALLALHLAHALRRA |

| | (SEQ ID NO: 5) |
|---|---|
| LAH4-L0: | KKALLAHALAHLALLALHLALHLKKA |

| | (SEQ ID NO: 6) |
|---|---|
| LAH4-L2: | KKALLALALHHLALLALHLAHALKKA |

| | (SEQ ID NO: 7) |
|---|---|
| LAH4-L3: | KKALLALALHHLALLAHHLALALKKA |

| | (SEQ ID NO: 8) |
|---|---|
| LAH4-L4iso: | KKALLHLALLHAALLAHHLALALKKA |

| | (SEQ ID NO: 9) |
|---|---|
| LAH4-L5: | KKALLHLALLHAALLAHLAALHLKKA |

| | (SEQ ID NO: 10) |
|---|---|
| LAH4-L6iso: | KKALLHLALLLAALHAHLAALHLKKA |

| | (SEQ ID NO: 11) |
|---|---|
| LAH4-A1: | KKALLAHALHLLAALALHLAHLLKKA |

| | (SEQ ID NO: 12) |
|---|---|
| LAH4-A2: | KKALLLAALHHLAALALHLAHLLKKA |

| | (SEQ ID NO: 13) |
|---|---|
| LAH4-A3: | KKALLLAALHHLLALAHHLAALLKKA |

| | (SEQ ID NO: 14) |
|---|---|
| LAH4-A4: | KKALLHAALAHLLALAHHLLALLKKA |

| | (SEQ ID NO: 15) |
|---|---|
| LAH4-A5: | KKALLHALLAHLAALLHALLAHLKKA |

| | (SEQ ID NO: 16) |
|---|---|
| LAH4-A6iso: | KKALLHALLAALLAHLHALLAHLKKA |

| | (SEQ ID NO: 17) |
|---|---|
| LAH4-A4-K1N: | KALLHAALAHLLALAHHLLALLKKA |

| | (SEQ ID NO: 18) |
|---|---|
| LAH4-A4-K3N: | KKKLLHAALAHLLALAHHLLALLKKA |

| | (SEQ ID NO: 19) |
|---|---|
| LAH4-A4-dKC: | KKALLHAALAHLLALAHHLLALLA |

| | (SEQ ID NO: 20) |
|---|---|
| LAH4-A4-d1aa: | KKALLHAALAHLLALAHHLLALLKK |

| | (SEQ ID NO: 21) |
|---|---|
| LAH4-A4-d2aa: | KKLLHAALAHLLALAHHLLALLKK |

| | (SEQ ID NO: 22) |
|---|---|
| LAH4-A4-d2Caa: | KKALLHAALAHLLALAHHLLALKK |

| | (SEQ ID NO: 23) |
|---|---|
| LAH4-A4-d3aa: | KKLHAALAHLLALAHHLLALLKK |

| | (SEQ ID NO: 24) |
|---|---|
| LAH4-A4-d5aa: | KKLHAALAHLLALAHHLLAKK |

| | (SEQ ID NO: 25) |
|---|---|
| LAH2-A6: | KKALLHAALAHLLALAAALLALLKKA |

| | (SEQ ID NO: 26) |
|---|---|
| K2-L10A12-K2: | KKALLAAALAALLALAAALLALLKKA |

| | (SEQ ID NO: 27) |
|---|---|
| LAH4-A4-Leu: | KKLLLHALLAHLLALLHHLLALLKKL. |

According to second aspect, the invention relates to novel LAH4-derived peptides. In this second aspect, the invention relates to a cationic amphipathic peptide comprising 19 or more amino acids, in particular 20, 21 or more amino acids. In a particular embodiment, the peptide comprises between 20 and 30 amino acids, in particular between 21 and 26, in particular between 24 and 26;

an N-terminal end comprising one or more amino acid residues positively charged at pH 7.4;

at least two histidine residues, in particular four histidine residues, defining a hydrophilic angle comprised between 80° and 180° in Schiffer-Edmundson's wheel representation, more specifically an angle of 140°;

the other amino acids of the peptide being selected between alanine and leucine residues;

wherein in Schiffer-Edmundson's wheel representation said peptide comprises only alanine residues between the most distant histidine residues in the smallest angle defined by said histidine residues.

These novel peptides of the second aspect are functional derivatives of the LAH4 peptide as defined above.

In a particular embodiment of the second aspect, the hydrophilic angle is comprised between 120 and 180°, the most preferred angle being 140°.

According to a particular embodiment of this second aspect, the N-terminal end of the peptide of the invention comprises one, two or three (in particular one or two) positive charge(s) at pH 7.4 (provided in particular by arginine or lysine residues, preferably lysine residues). The positively charged residues are preferably located at the extremity of the N-terminal end, and preferably contiguously if more than one positively charged residues are present.

In another particular embodiment of the second aspect, the peptide of the invention presents a C-terminal end comprising one or more amino acid residues positively charged at pH 7.4. Representative residues that can provide positive charges in the C-terminal end are arginine and/or lysine residues.

In a further embodiment of the second aspect, the C-terminal residue is an alanine and in a further aspect, when the C-terminal end of the peptide comprises positively charged amino acid residues at pH7.4, they are located next to the C-terminal alanine or located at the most N-terminal extremity.

According to another particular embodiment of the second aspect, the peptide of the invention comprises four histidine residues. In a specific embodiment, said histidine residues form two pairs of adjacent histidines in a α-helix represented according to the Schiffer-Edmundson's wheel.

In a further embodiment of the second aspect, the LAH4-derived peptide is an isomer of the LAH4 peptide, i.e. it contains the same number of alanine, histidine, leucine and lysine residues, in a different order in the primary sequence.

Representative peptides of the second aspect covered by this definition are shown in SEQ ID NOs: 11-25 and 27. The invention thus relates to a peptide selected in the group consisting of SEQ ID NOs: 11-25 and 27.

In a third aspect, the invention relates to novel LAH4-derived peptides comprising:

19 or more amino acids, in particular 20, 21 or more amino acids. In a particular embodiment, the peptide comprises between 20 and 30 amino acids, in particular between 21 and 26, in particular between 24 and 26;

a N-terminal end comprising one or more amino acid residues positively charged at pH 7.4;

an apolar helix harboring a cluster of hydrophobic amino acid residues on one side of the helix and consecutive alanine residues on the other side of the helix defining an angle of 60 to 180° in Schiffer-Edmundson's wheel representation and preferentially an angle of 140°.

In a particular variant of this third aspect, the other amino acids of the peptide are selected between alanine and leucine residues.

These novel peptides of the third aspect are functional derivatives of the LAH4 peptide as defined above.

These peptides contain an apolar helix, i.e. the amino acids residues of the helix are hydrophobic (or apolar). Representative hydrophobic amino acid residues preferably contained in the apolar helix of the peptide of the invention comprise alanine, isoleucine, leucine and valine residues, in particular alanine and leucine residues.

In a particular embodiment of the third aspect, the amino acids in the cluster of hydrophobic amino acids are selected in the group consisting of leucine and alanine residues. In another particular embodiment, the amino acids in the cluster of hydrophobic amino acids are leucine residues.

Peptide K2-L10A12-K2 (SEQ ID NO:26) is a representative peptide according to this definition.

According to a particular embodiment of the third aspect, the N-terminal end of the peptide of the invention comprises one, two or three (in particular one or two) positive charge(s) at pH 7.4 (provided in particular by arginine or lysine residues, preferably lysine residues). The positively charged residues are preferably located at the extremity of the N-terminal end, and preferably contiguously if more than one positively charged residue is present.

In another particular embodiment of the third aspect, the peptide of the invention presents a C-terminal end comprising one or more amino acid residues positively charged at pH 7.4. Representative residues that can provide positive charges in the C-terminal end are arginine and/or lysine residues.

In a further embodiment of the third aspect, the C-terminal residue is an alanine and in a further aspect, when the C-terminal end of the peptide comprises positively charged amino acid residues at pH7.4, they are located next to the C-terminal alanine or located at the most N-terminal extremity.

According to a fourth aspect, the invention relates to a cationic amphipathic peptide which is a LAH4 functional derivative, comprising 19 or more amino acids, in particular 20, 21 or more amino acids. In a particular embodiment, the peptide comprises between 20 and 30 amino acids, in particular between 21 and 26, in particular between 24 and 26;

an N-terminal end comprising one or more amino acid residues positively charged at pH 7.4;

at least two histidine residues, preferably four histidine residues, defining a hydrophilic angle comprised between 140° and 180° in Schiffer-Edmundson's wheel representation, more specifically an angle of 140°;

wherein in Schiffer-Edmundson's wheel representation said peptide comprises only leucine residues between the most distant histidine residues in the smallest angle defined by said histidine residues.

In a particular embodiment of this fourth aspect, the other amino acids of the peptide are selected from alanine and leucine residues.

The peptide of this fourth aspect is not the LAH4-L4 peptide of SEQ ID NO:36 and is not the LAH4-L6 peptide of SEQ ID NO:37.

In a particular embodiment of this fourth aspect, the peptide of the invention is an isomer of the LAH4 peptide of SEQ ID NO:1, whose amino acid sequence consists of 8 alanine, 4 histidine, 10 leucine and 4 lysine residues.

According to a particular embodiment of this fourth aspect, the N-terminal end of the peptide of the invention comprises one, two or three (in particular one or two) positive charge(s) at pH 7.4 (provided in particular by arginine or lysine residues, preferably lysine residues). The positively charged residues are preferably located at the extremity of the N-terminal end, and preferably contiguously if more than one positively charged residue is present.

In another particular embodiment of the fourth aspect, the peptide of the invention presents a C-terminal end comprising one or more amino acid residues positively charged at pH 7.4. Representative residues that can provide positive charges in the C-terminal end are arginine and/or lysine residues.

In a further embodiment of the fourth aspect, the C-terminal residue is an alanine and in a further aspect, when the C-terminal end of the peptide comprises positively charged amino acid residues at pH7.4, they are located next to the C-terminal alanine or located at the most N-terminal extremity.

Representative peptides covered by this fourth aspect include peptides LAH4-L4 iso, LAH4-L5 and LAH4-L6 iso (SEQ ID NOs: 8-10). Accordingly, the present invention also relates to a peptide selected in the group consisting of SEQ ID NOs: 8-10.

Several methods for producing the peptides of the invention are available and known to the skilled person. According to a first method, a nucleic acid sequence coding a peptide of the invention is expressed in bacteria such as *E. coli* or any other expression system. The peptide is then purified according to conventional methods. According to a second method, the peptide is synthesized using a synthesizer (see for example Bechinger, 1996).

The peptides of the invention are derived from the LAH4 peptide. While the latter is recognized as promoting the transfection of nucleic acids in eukaryotic cells, its advantageous properties on promoting virus transduction has never been disclosed or suggested. Here, the inventors show that the LAH4 peptide and derivatives thereof promote viral infection of a target cell and enhance the infectivity of cells by viruses.

Further embodiments of the invention are peptides derived from LAH4 peptide or their functional derivatives as outlined above with at least one of the following covalent modifications:

acylation, acetylation, linkage to a non-peptidic macromolecular carrier group; preferably at the N-terminus;
amidation, linkage to a non-peptidic macromolecular carrier group; preferably at the C-terminus;
glycosylation; preferably at amino acid side chains;
linkage to an adaptor protein, which promotes uptake of the peptide into cells or linkage to a hydrophobic group, preferably a lipid, a fatty acid, a dansyl, a carbobenzoxyl or a t-butyloxycarbonyl group;
oxidation, sulphatization, esterification, lactone formation and/or phosphorylation.

The invention also covers multimers, for example dimers or trimers, of the peptides described above. In the context of the present invention, a "multimer" denotes functional LAH4 peptides that have been covalently linked together. Dimers, which are two functional LAH4 peptides linked together, may be for example obtained by introduction of thiol groups at the C or N-terminus— these groups can then be used to generate dimers by formation of a disulfide bridge. Other reagents can of course also be used to generate such multimers.

According to the invention, the LAH4 peptide or a functional derivative thereof (e.g., any one of SEQ ID NOs: 1-27) is amidated at its C-terminus or is not modified at the C-terminus. Preferred macromolecular carrier groups are polyethylene glycol (PEG), polyoxyalkylene glycol, polysorbate esters, mannan, amylopectin, pullulan, hydrogel-nanoparticles of self aggregated hydrophobized polysaccharides, polylysine, antibodies or albumine.

According to a particular embodiment, the invention also encompasses retro, inverso or retro-inverso derivatives of the peptides defined above, which retain the transduction promoting properties herein disclosed. The peptides may comprise at least one D amino acid as well as iminoamino acids and rare amino acids. The invention also relates to peptide mimetics of the peptides according to the invention. These can be characterized for example by a modification of one or more peptide bonds, for example, by a reverse peptide bond or by an ester bond. But it includes also peptides with beta or gamma-amino acids, etc. . . .

The peptides of the invention promote viral infection of a cell. As used herein, "viruses" relates to natural occurring viruses as well as artificial viruses. For example, paramyxovirus (such as respiratory syncytial virus, measle virus), orthomyxovirus (such as influenza virus), flavivirus (such as hepatitis C virus), hepadnavirus (such as hepatitis B virus), rhabdovirus (such as rabies, VSV), coronavirus (such as SARS), togavirus (such as Sindbis virus, Chikungunya virus), filovirus (such as ebola virus), arenavirus, poxvirus, herpesvirus, bunyavirus, bornavirus, arterivirus, baculovirus. According to a particular embodiment, the viruses are artificial viruses, which may for instance comprise a nucleic acid designed for gene therapy. In a preferred embodiment, the viruses are enveloped viruses. In preferred embodiments, the viruses are retroviruses and in particular lentiviruses. The inventors have shown that peptides of the present invention can promote the infection of eukaryotic cells with HIV-1 derived lentiviral vectors (LVs) comprising pseudotyped envelopes with glycoproteins from vesicular stomatis virus (VSV), modified feline endogenous retrovirus (RD114), amphotrophic murine leukemia virus (MLV), modified gibbon ape leukemia virus (GALV) and even with glycoproteins from AcMNPV baculovirus (GP64), the latter being a virus normally specific for insect cells. In view of the efficiency of the transduction obtained with the peptides of the invention and the diversity of the glycoproteins used in the disclosed experiments, it is clear that the present peptides can be used as a general means for increasing transduction efficiencies of enveloped viruses in eukaryotic cells.

The target cells can be any kind of eukaryotic cells such as mammalian cells, in particular human, mouse, rat, monkey, dog or hamster cells. In a particular embodiment, the target cell is a CD34+ cell, in particular a CD34+ cell collected from a patient in need of a gene therapy of his/her hematopoietic lineage. Other representative, non-limiting, target tissues/cells are skin, muscle, liver, eye, neurons, lymphocytes, fibroblasts, keratinocytes, adipocytes, myoblasts, hepatocytes, tumor cells and more generally any eukaryotic cell that is known or will be identified as a target of a virus.

The activity of the peptides with a given virus and given target cell can be measured using a reporter assay, for instance using a luciferase assay or a GFP expression assay as provided in the examples. In particular, the peptides can be tested according to the following method:

the cells (e.g. HCT116 cells or 293T cells) are plated in a culture dish, for example a 12-well plate (e.g. at $10^5$ cells/well) and maintained overnight at 37° C.;
viruses comprising a GFP transgene are incubated in absence or presence of various concentrations of peptides (e.g. 3, 6 and/or 12 µg/ml) during 15 min at 37° C.;
the viruses, either alone or in mixture with the peptides, are then mixed with the cells;

optionally, after a time sufficient for the infection to occur, for example 6 hours after the previous step, the medium can be removed and replaced by fresh culture medium; the cells are further cultured 2 to 3 days;

the transduction efficiency is determined by monitoring GFP expression using adapted means, for example flow cytometry.

A method for identifying peptides useful for promoting the transduction of a cell by an (enveloped) vector is also part of the invention. This method may implement the steps provided in the previous paragraph for identifying peptides that enhance viral infection into cells at least by a factor of 2, more preferably by a factor of 3, 5 or 10 when compared to viral infection into the cells in the absence of the peptide.

In the uses and methods of the present invention, the LAH4 peptide and functional derivatives thereof are used in an effective amount. In the present invention, the term "effective amount" of the peptide denotes the amount required for increasing significantly the transduction efficiency of a viral vector. This effective amount will generally depend on the particular peptide tested, the target cell and the viral vector implemented. This amount can be determined according to methods well known in the art, in particular according to the above method implementing a reporter assay and illustrated in the examples. For example, the inventors have shown that the optimal concentration of LAH4-L1 necessary to promote CD34+ cells transduction with GALVTR-LV is around 12 μg/ml (final concentration in transduction medium).

According to a further aspect, the invention relates to a complex of a LAH4 peptide or a functional derivative thereof with a virus particle, in particular an enveloped virus particle, more particularly with an enveloped viral vector for gene therapy. Moreover, another aspect of the invention relates to a method for preparing such complex, which comprises mixing the peptide with a viral particle.

According to another aspect, the invention relates to a mixture of a LAH4 peptide or a functional derivative thereof with a virus particle (in particular an enveloped virus particle, more particularly with an enveloped viral vector for gene therapy) and with a cell. Moreover, another aspect of the invention relates to a method for preparing such mixture, which comprises mixing the peptide, with the viral particle and the cell.

The peptides according to the invention can be used in pharmaceutical compositions. Thus, the present invention relates to a composition comprising a peptide as defined above and a suitable pharmaceutically acceptable vehicle. The pharmaceutical compositions of the invention contain one or more of the peptides according to the invention, or a physiologically acceptable salt of the peptide(s). Pharmaceutical compositions according to the invention can also contain pharmaceutically usual auxiliary agents which contribute, for example, to the solubility, stability or sterility of the composition or increase the efficiency of uptake into the body.

An aspect of the invention also relates to a peptide as defined above, for use as a medicament. In a particular embodiment, the medicament is used for increasing the efficiency of a gene therapy viral vector (D'Costa et al., 2009).

The form and content of the pharmaceutical composition which contains the peptide(s) depends on the route of administration. Preferably, galenic formulations and application forms are selected in which the peptide(s) arrive(s) at the target site in a non-degraded condition. The medicament can be administered locally as injection, drops, spray, tablets, suppositories, cream, ointments, gel etc. It is possible to perform the administration as a bolus or repeatedly over a period of time.

The peptide, complex or pharmaceutical composition or medicament of the invention can be administered in vivo, for example by injecting it via the intramuscular, intravenous, intra-arterial, intra-peritoneal or intracranial route. The invention thus also relates to a method for gene therapy, comprising administering to a patient in need thereof a peptide, complex or pharmaceutical composition as described above. The method comprises also administering a virus vector for gene therapy before, after or together with the administration of the peptide of the invention.

In a particular aspect, the invention also relates to a composition comprising a peptide as described above in a culture medium, said composition being intended for use as an infection promoting reagent for facilitating the transduction of a cell with a virus or viral vector, in particular an enveloped virus or viral vector. Thus, the invention also relates to a virus infection promoting reagent comprising a peptide according to the present invention, in a suitable medium, in particular in a suitable culture medium.

According to another aspect, herein disclosed is the use of the LAH4 peptide or a functional derivative thereof as an antibiotic.

According to another aspect, herein disclosed is the use of a LAH4 functional derivative as a cell penetrating peptide (CPP). In particular, the peptide is used as a delivery system for bioactive compounds such as nucleic acid, for example plasmid DNA, siRNAs, antisense oligonucleotides, and other bioactive compounds (peptides or proteins, in particular therapeutic peptides or proteins, marker peptides, antibodies, etc.) The CPP can be either covalently or non covalently linked to the bioactive compound. In a particular embodiment, the peptide is a LAH4 peptide functional derivative.

According to another aspect, the invention also provides nucleic acids coding for the peptides of the invention and expression vectors for the inventive peptides, such as plasmids, cosmids and viral vectors.

The peptides described herein are used for a broad range of therapeutic and diagnostic applications and are valuable laboratory tools for the performance and study of entry of viruses into cells.

A preferred embodiment of the invention is the use of the LAH4 peptide or a functional derivative thereof as general enhancer of viral infection or transduction efficiencies for routine laboratory practice or gene therapeutic approaches based on viral vector systems. The peptides are enhancing the entry of vectors designed for gene therapy into cells in vitro, ex vivo or in vivo. They may be administered in combination with a viral vector for gene therapy and mediate entry of the viral vector into the target cell. The peptides are also useful in vitro because they promote the uptake of viruses into cells. They are thus useful as a tool for studying viruses and their mechanisms of action. Another embodiment of the invention is the use of the LAH4 peptide or functional derivatives thereof for diagnostic approaches, especially those of viruses like HIV-1 and other enveloped viruses. The LAH4 peptide and functional derivatives thereof enhance the infectious titers of virus particles and therefore enhance the cellular uptake, allowing the detection of residual viral contaminations. Therefore, they can be used to isolate viral particles from samples like serum, blood, plasma, sperm or tissues derived from subjects, in particular a human subject suspected to be infected by a virus, more specifically by an enveloped virus. The peptides according to the invention can also be used to study viral particles from water, food (avian influenza, SARS) or any (enveloped) virus used in bioterrorism. Successful virus isolation could be favored several times compared with routine diagnostic methods. Preferred methods are binding affinity assays and methods to remove viruses quantitatively from solutions suspected or known to comprise viruses in order to obtain safe solutions. In such methods, the peptides of the invention are preferably covalently bound to a support or a column.

The invention also relates to polynucleotides coding for the peptides according to the invention, such polynucleotides being preferably constituted of DNA, RNA, genomic DNA or PNA. Another aspect of the invention relates to vectors containing the polynucleotide according to the invention, and genetically engineered host cells containing the vector according to the invention.

The peptides of the invention can be used to enhance in general the entry of virus particles into target cells. The peptides can also be used as a general enhancer of the infection/transduction rate of enveloped viral particles that carry foreign envelope glycoproteins (pseudoparticles) like the G protein of the Vesicular Stomatitis Virus (VSV-G), the Env protein of MLV, etc. The above peptides of the invention promote the infection rates of all analyzed enveloped virus particles. This allows us to perform infection experiments, especially in primary cells, that have not been feasible before. The peptides of the invention are thus useful as laboratory tools in vitro.

The peptides of the invention can also be used to enhance gene delivery rates in ex vivo or in vivo gene therapy approaches based on vector systems, in particular on enveloped vector systems. Accordingly, the invention also relates to a peptide is described above for use in gene therapy for promoting the infection of an eukaryotic cell by a virus or a viral vector in a subject in need thereof. The peptide of the invention can be used in combination with a virus or viral vector in gene therapy. The peptide may be for the simultaneous, separate or sequential administration with the gene therapy vector. The generation of highly infectious retroviral vectors for gene therapy, especially for ex vivo gene therapy of stem cells, is a difficult procedure. In particular, the transduction efficiencies of retroviral vectors for stem cells are low. In the presence of the peptides of the invention, however, stem cells and cell lines can be efficiently transduced with retroviral vectors, resulting in higher efficiencies for gene delivery into the target cell compared to samples containing no peptide.

In the in vitro and ex vivo methods of the present invention, the peptide can be used either with or without prior immobilization on a solid support. Advantageously, no immobilization is required for obtaining an increased transduction efficiency.

In a particular embodiment of the in vitro methods of the invention, another transduction improving means is used together with the LAH4 peptide or functional derivative thereof. For example, in a particular embodiment, transduction efficiency is increased with both a peptide according to the invention and with Retronectin or a SEVI peptide.

In another embodiment, the invention provides a kit comprising a peptide as defined above and a virus or viral vector.

The invention is further described by means of the following examples.

LEGEND TO THE FIGURES

FIG. 1. Capacity of LAH4-L1 to enhance infectious LV titers. A) GALVTR-LVs, MLV-A-LVs, RD114TR-LVs, VSV-G-LVs and VLPs were used to transduce HCT116 cells (1.2×10E5 TU/ml or 200 ng/ml of HIV-1 p24 for VLPs). GP64-LVs were used to transduce 293T cells (0.8×10E5 TU/ml). Transductions were performed in absence or presence of 3, 6 or 12 μg/ml of LAH4-L1. Data are shown as GFP+ cell percentages with standard deviations (SD) of triplicate conditions. B) Data obtained in (A) are represented as the fold of enhancement mediated by LAH4-L1 with the mock condition normalized to one.

FIG. 2. Determination of the optimal concentration of LAH4-L1 to promote human CD34+ cells transduction with GALVTR-LVs. A) Pre-activated hCD34+ cells were transduced with GALVTR-LVs (2×10E6 TU/ml, MOI 16) pre-incubated or not with various concentrations of LAH4-L1. Transduction efficiencies (black squares) are represented as the percentages of GFP+ cells obtained 5 days post-transduction. The mortality (gray circles) was estimated two days post-transduction after cellular DNA labeling with 7-AAD. B) hCD34+ cells were transduced with two different doses of GALVTR-LVs (1 and 2×10E6 TU/ml, MOI 8 and 16) pre-incubated or not with the optimal concentration of LAH4-L1 (12 μg/ml). Data are obtained from six different cord blood donors (three donors for each GALVTR-LV doses). Bars indicate the mean value of the distributions.

FIG. 3. Evaluation of the safety of LAH4-L1 in the "Human Immune System" (BALB-Rag/γC) mice model.

Prior to injection into seven rag−/−/γC−/− mice from the same littermate, hCD34+ cells were left untransduced (triangle) or were transduced with GALVTR-LVs (MOI 8) either in presence of 12 μg/ml of LAH4-L1 (square) or 20 $\mu g/cm^2$ of Retronectin (circle). A) Twelve weeks post-injection, effective engraftment level of HIS (BALB-Rag/γC) mice was monitored by following the percentages of transduced (GFP+) hCD45+ cells in the blood, the bone marrow (BM), the spleen and the thymus using flow cytometry. B and C) Study of human T lymphopoiesis in vivo in the thymus by following the human TCRα/β marker expression in the hCD45+ cell subset and the human CD4 and CD8 markers expression in the hCD3+ cell subset. T lymphopoiesis is analyzed either in untransduced (B) or transduced cells (C). D to G) Study of human B lymphoid development, human monocytes and human natural killer cells in vivo in the spleen (D and E) and the BM (F and G) by following respectively the human CD19, CD14 and CD56 marker expression in the untransduced (D and F) or transduced (E and G) hCD45+ cell subset. Human hematopoietic progenitors are also analyzed in the BM by following the human CD34 marker expression in the hCD45+ cell subset.

FIG. 4. Transduction of human CD34+ cells with GALVTR-LVs in presence of LAH4-L1 derivatives. A) Table of peptide sequences of various LAH4-L1 derivatives (D-LAH4-L1 sequence is identical to LAH4-L1 but with D-amino acids). B) hCD34+ cells were transduced with GALVTR-LVs (10E6 TU/ml, MOI 8) either pre-incubated or not (Mock) with LAH4-L1 or different LAH4-L1 derivatives (12 μg/ml). Transduction efficiencies are expressed as percentages of LAH4-L1 control condition. C) The mortality was estimated two days post-transduction after cellular DNA labeling with 7-AAD. Data are the average of two independent experiments performed in duplicate with SD.

FIG. 5. Transduction of human CD34+ cells with GALVTR-LVs in presence of LAH4-L1 isomers. Table of peptide sequences of the L series (A) and the A series (D) of LAH4-L1 isomers. B and E) Schiffer-Edmundson's helical wheel representation of the amphipathic α-helical region (aa6 to aa23) of LAH4-L1 isomers. The peptide name and the polar angle formed by the hydrophilic Histidine residues (underline) are mentioned inside the wheel projection. C and F) hCD34+ cells were transduced with GALVTR-LVs (10E6 TU/ml, MOI 8) either pre-incubated with 12 µg/ml of LAH4-L1 or different LAH4-L1 isomers of the L series (C) or the A series (F). Transduction efficiencies are represented as the percentages of GFP+ cells obtained 5 days post-transduction. Data are expressed as the average of two independent experiments performed in duplicate with SD.

Figure 6:
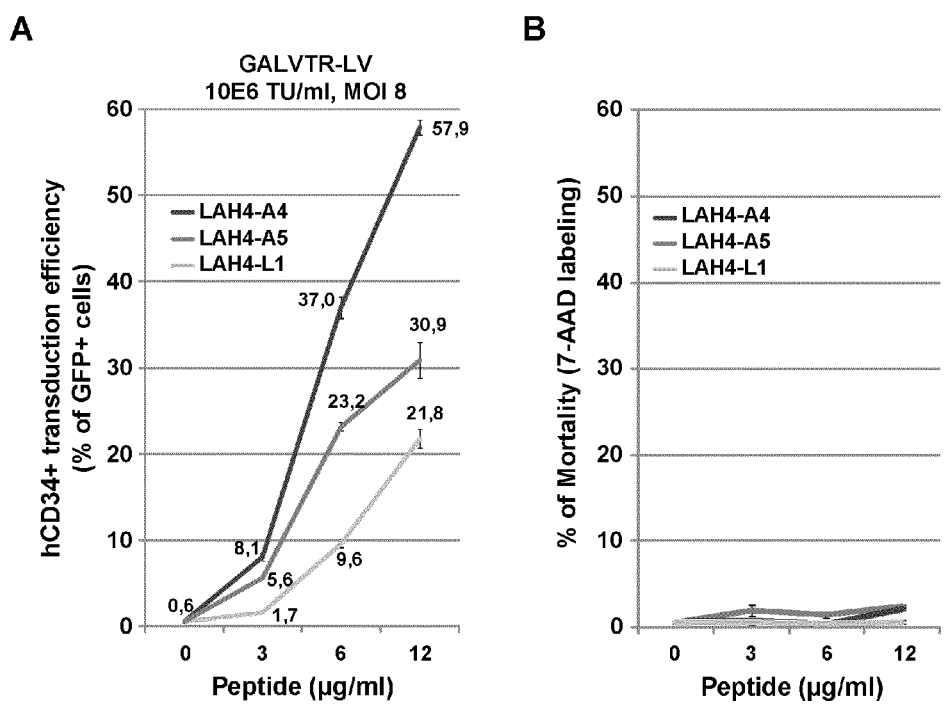

FIG. 6. Dose-response curves of LAH4-L1, LAH4-A4 and LAH4-A5 on the transduction of human CD34+ cells with GALVTR-LVs. A) hCD34+ cells were transduced with GALVTR-LVs (10E6 TU/ml, MOI 8) pre-incubated or not with various concentrations of LAH4-L1, LAH4-A4 and LAH4-A5 (3, 6 and 12 µg/ml). Transduction efficiencies are represented as the percentages of GFP+ cells with SD obtained 5 days post-transduction. B) The mortality was estimated as in FIG. 4C.

Figure 7:
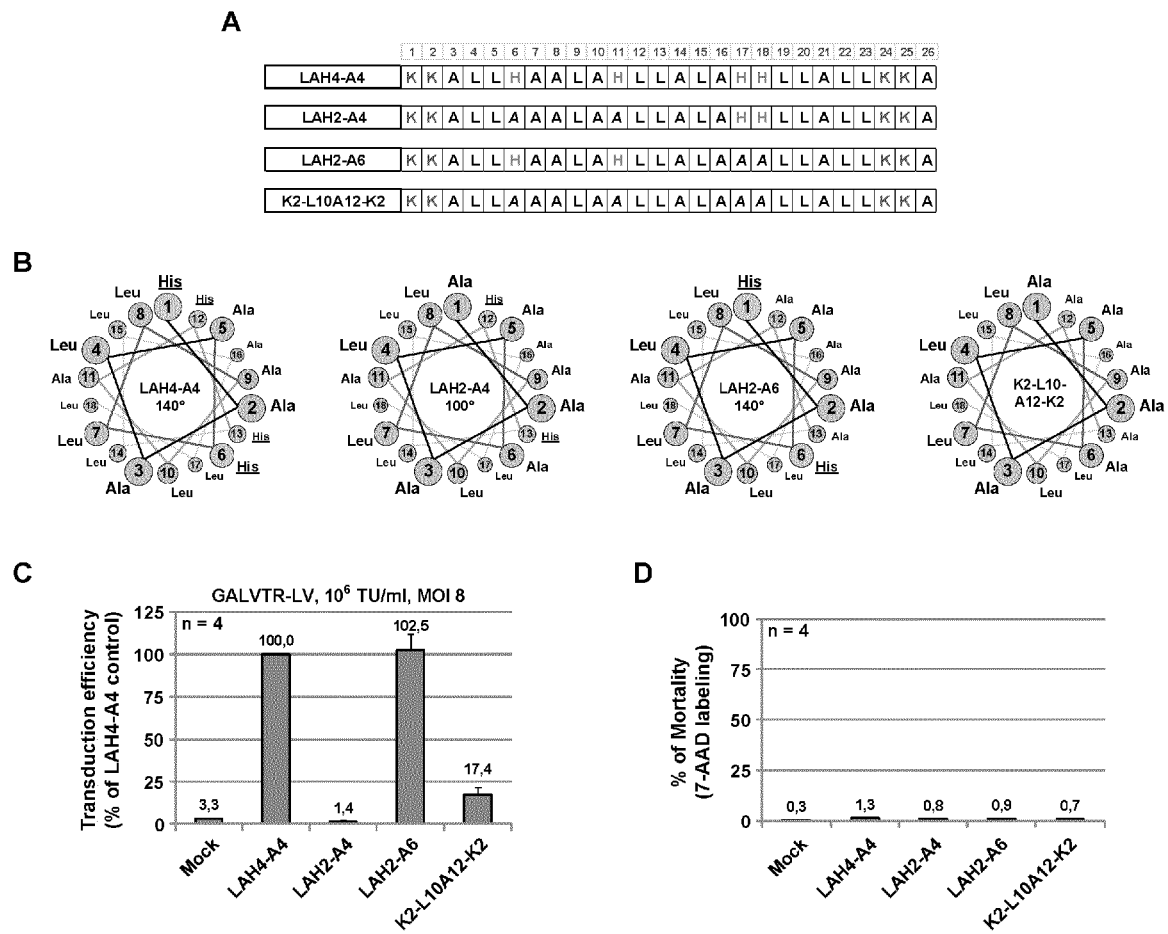

FIG. 7. Transduction of human CD34+ cells with GALVTR-LVs in presence of LAH4-A4 histidine derivatives. A) Table of peptide sequences of LAH4-A4, LAH2-A4, LAH2-A6 and K2-L10A12-K2. B) Schiffer-Edmundson's helical wheel representation of the amphipathic α-helical region (aa6 to aa23) of LAH4-A4 histidine derivatives. The peptide name and the polar angle formed by the hydrophilic Histidine residues (underline) are mentioned inside the wheel projection. C) hCD34+ cells were transduced with GALVTR-LVs (10E6 TU/ml, MOI 8) either pre-incubated with LAH4-A4 or different LAH4-A4 histidine derivatives (12 µg/ml). Transduction efficiencies are expressed as percentages of LAH4-A4 control condition. D) The mortality was estimated as in FIG. 4C. Data are the average of two independent experiments performed in duplicate with SD.

Figure 8:
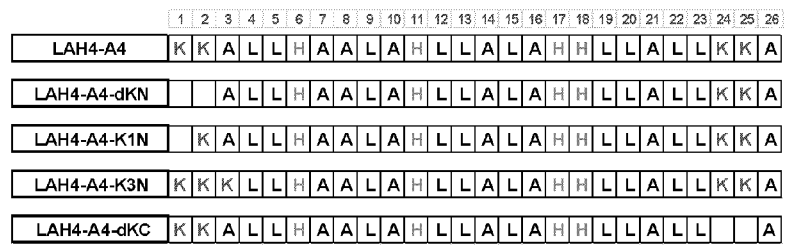
Figure 8:
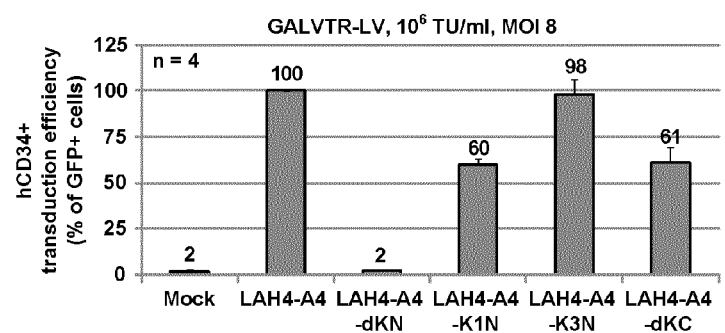
Figure 8:
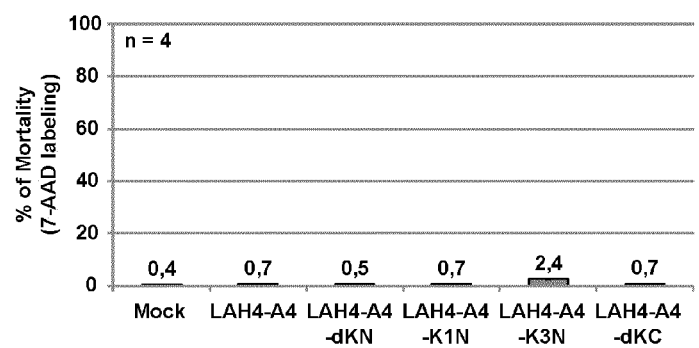

FIG. 8. Transduction of human CD34+ cells with GALVTR-LVs in presence of LAH4-A4 lysine derivatives. A) Table of peptide sequences of LAH4-A4, LAH4-A4-dKN, LA4-A4-K1N, LAH4-A4-K3N and LAH4-A4-dKC. B) hCD34+ cells were transduced with GALVTR-LVs (10E6 TU/ml, MOI 8) either pre-incubated with LAH4-A4 or different LAH4-A4 lysine derivatives (12 µg/ml). Transduction efficiencies are expressed as percentages of LAH4-A4 control condition. C) The mortality was estimated as in FIG. 4C. Data are the average of two independent experiments performed in duplicate with SD.

Figure 9:
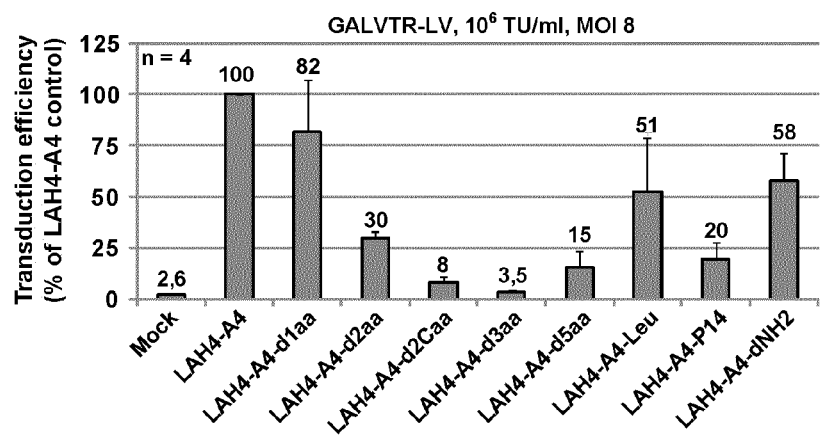
Figure 9:
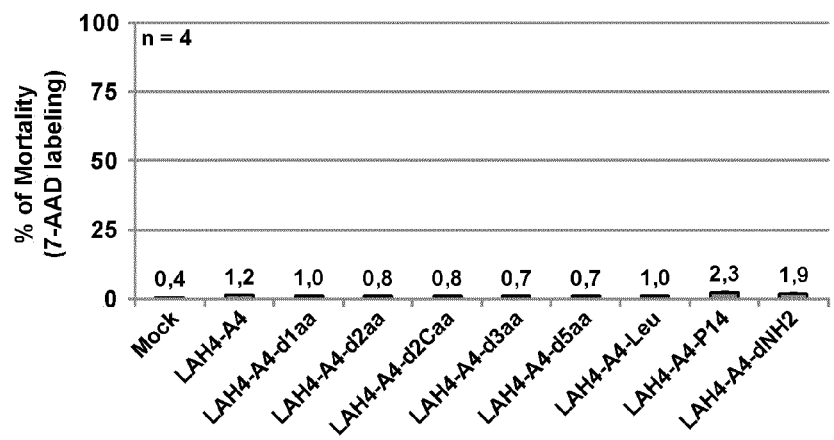

FIG. 9. Transduction of human CD34+ cells with GALVTR-LVs in presence of various LAH4-A4 derivatives. A) Table of peptide sequences. B) hCD34+ cells were transduced with GALVTR-LVs (10E6 TU/ml, MOI 8) either pre-incubated with LAH4-A4 or different LAH4-A4 derivatives (12 µg/ml). Transduction efficiencies are expressed as percentages of LAH4-A4 control condition. C) The mortality was estimated as in FIG. 4C. Data are the average of two independent experiments performed in duplicate with SD.

Figure 10:
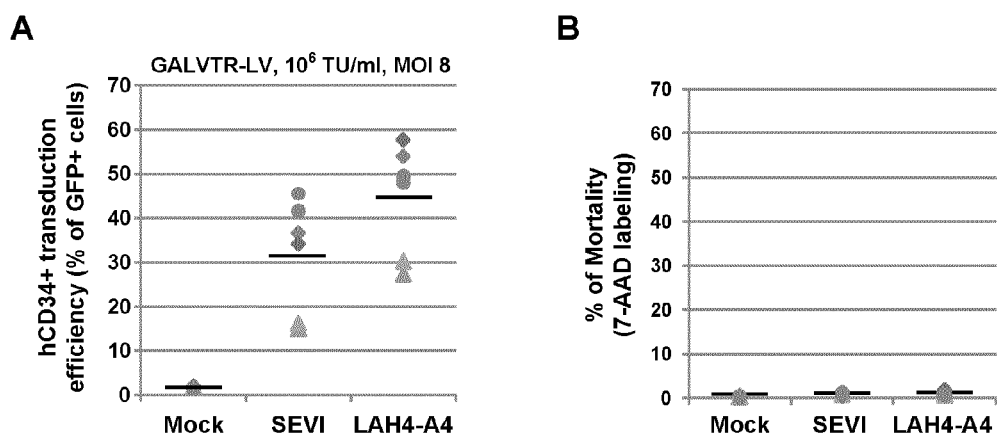

FIG. 10. Transduction of human CD34+ cells with GALVTR-LVs in presence of LAH4-A4 or SEVI peptides. A) hCD34+ cells were transduced with GALVTR-LVs (10E6 TU/ml, MOI 8) either pre-incubated with LAH4-A4 (12 µg/ml, 2.2 µM) or SEVI peptide (20 µg/ml, 2.2 µM). Transduction efficiencies are represented as the percentages of GFP+ cells obtained 5 days post-transduction. B) The mortality was estimated as in FIG. 4C. Data are obtained from three different cord blood donors in duplicate. Bars indicate the mean value of the distributions.

Figure 11:
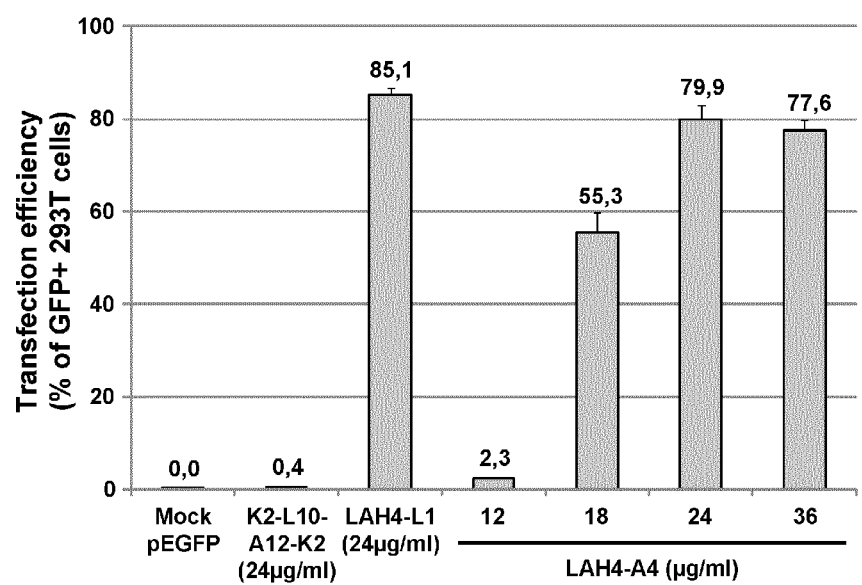

FIG. 11. Transfection of 293T cells with pEGFP in presence of LAH4-A4, LAH4-L1 or K2-L10A12-K2 peptides. pEGFP-C1 plasmid (1 µg) was mixed in 50 µl of 150 mM NaCl solution with either 3 µg, 4.5 µg, 6 µg or 9 µg of LAH4-A4 or 6 µg of LAH4-L1 or 6 µg of K2-L10A12-K2. Next, the DNA/peptide mix was diluted in 200 µl of DMEM without FCS and loaded onto cell monolayers. 3 hours post-transfection, the medium was replaced with DMEM containing 10% FCS. 48 h later, transfection efficiencies were estimated by monitoring GFP expression using flow cytometry. Data are the average of two independent experiments performed in duplicate with SD.

Figure 12:
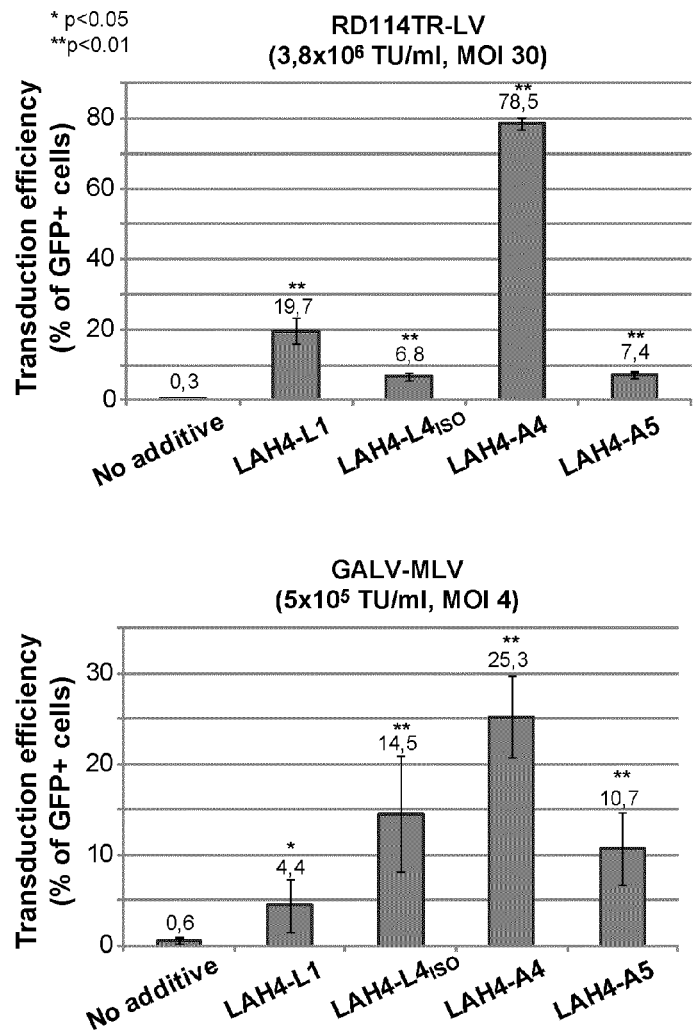

FIG. 12. Effect of LAH4-A4 on RD114TR-LVs and GALV-MLVs pseudotypes. hCD34+ cells were transduced with raw supernatants of either RD114TR-LVs (3.8×10E6 TU/ml) or the moloney retroviral vector GALV-MLVs (5×10E5 TU/ml) in absence or presence of 12 µg/ml of LAH4-L1, LAH4-L4$_{ISO}$, LAH4-A4 or LAH4-A5 peptides. Transduction efficiencies are represented as the percentage of GFP+ cells with SD obtained 5 days post-transduction. Data are obtained from two different cord blood donors in duplicate for RD114TR-LV or three different cord blood donors in simplicate for GALV-MLV.

EXAMPLES

Materials and Methods
Peptides and Reagents

Peptides were produced by standard Fmoc solid-phase peptide synthesis, purified by preparative RP HPLC and analyzed by HPLC and MS (Genecust, Dudelange, Luxembourg). All the peptides were amidated at their C-terminal end, except LAH4-A4-dNH2 and SEVI. 7-amino-actinomycin D (7-AAD) was obtained from Sigma-Aldrich (St Quentin Fallavier, france). Retronectin was from Takara Bio Inc. (St-Germain-en-laye, France). pEGFP-C1 plasmid was from Clontech (St-Germain-en-laye, France). Antibodies were from Miltenyi (Paris, France).

In addition to the peptides represented in SEQ ID NOs: 1-27, the following peptides have also been used in the present study:

```
                                            (SEQ ID NO: 28)
LAH4-A4-    KKALLHAALAHLLPLAHHLLALLKKA.
P14:

(SEQ ID NO: 29)
LAK4-L1:    KKALLAKALKLLALLALKLAKALKKA (SEQ ID NO: 30)
LAH8-L1:    HHALLAHALHLLALLALHLAHALHHA (SEQ ID NO: 31)
LAH4-L1-    ALLAHALHLLALLALHLAHALA
dK:

(SEQ ID NO: 32)
LAH4-L1-    ALLAHALHLLALLALHLAHALKKA
dKN:

(SEQ ID NO: 33)
LAH4-A4-    ALLHAALAHLLALAHHLLALLKKA
dKN:

(SEQ ID NO: 34)
LAH2-A4:    KKALLAAALAALLALAHHLLALLKKA (SEQ ID NO: 35)
SEVI:       GIHKQKEKSRLQGGVLVNEILNHMKRATQIPSYKKLIMY
```

Cell Line Culture

HCT116 cells derived from a human colorectal carcinoma (CCL-247, ATCC, Manassas, Va., USA) and 293T cells (Merten et al, 2011) were cultured at 37° C., 5% CO2 in Dulbecco's modified Eagle's medium (DMEM+Glutamax, Invitrogen/Gibco, Cergy-Pontoise, France) supplemented with 10% heat inactivated fetal calf serum (FCS) (Invitrogen/Gibco).

Viral Vector Production and Vector Titering

HIV-1 derived lentiviral vectors (LVs) were generated by transient calcium phosphate transfection of 293T cells with four plasmids: the transfer vector plasmid expressing GFP (pCCLsin-cPPT-hPGK-eGFP-WPRE) (Follenzi et al, 2000), the plasmid encoding HIV-1 Rev (pK.Rev) (Merten et al, 2011), the plasmid encoding HIV-1 gagpol (pKLgagpol) (Merten et al, 2011), and the appropriate envelope glycoprotein (GP) construct: pMDG (vesicular stomatitis virus GP (Naldini et al, 1996)) to generate VSV-G-LVs; pHCMV-RD114TR (modified feline endogenous retrovirus GP (Sandrin et al, 2002) to generate RD114TR-LVs; pBA-Ampho (amphotropic murine leukemia virus GP) to generate MLV-A-LVs, pBA_AcMNPV_gp64 (baculovirus GP) to generate GP64-LVs and pBA-GALVampho-Kana (modified gibbon ape leukemia virus GP (Sandrin et al, 2002) to generate GALVTR-LVs. Viral supernatants were collected 48 h post-transfection, filtered (0.45 µ), aliquoted and stored at −80° C. Infectious titers were determined by flow cytometry (FacsCalibur, BD Biosciences, San Jose, Calif., USA) as described previously (Kutner et al, 2009). Briefly, HCT116 cells were transduced with serial dilutions of vector stock, washed and 3 days later, transduction efficiencies were determined by monitoring GFP expression. For hCD34+ cells transduction, the final titer was expressed as transducing units per milliliter (TU/ml) and the multiplicity of infection (MOI) was defined. Physical particle titers were determined by measuring HIV-1 p24 capsid contents (ng/ml) using a commercial ELISA kit (PerkinElmer life science, Boston, Mass., USA).

Viral supernatants of MLV retroviral vector pseudotyped with GALV envelope glycoproteins were obtained from the producer cell line PG13-MFG-GFP (Merten 2004).

Cell Line Transduction

HCT116 cells (293T cells for transduction with GP64-LVs) were plated in 12-well plates ($10^5$ cells/well). The next day, LVs were incubated in absence or presence of various concentrations of LAH4-L1 (3, 6 or 12 µg/ml) during 15 min at 37° C. Next, LVs were loaded onto cell monolayers. 6 hours post-transduction, cells were washed and further cultured for 2 to 3 days. Transduction efficiencies were determined by monitoring GFP expression using flow cytometry.

Human CD34+ Cells Source, Culture and Transduction

Umbilical cord blood progenitor CD34+ cells were obtained by immunomagnetic selection (Miltenyi Biotec, Paris, France) from mononuclear cell fractions of cord blood samples obtained from uncomplicated births at Hopital Louise Michel, Evry, France, in compliance with French National Bioethics law. First, hCD34+ cells were pre-activated overnight in X-vivo 20 medium (Lonza, Levallois Perret, France) supplemented with cytokines as described previously (charrier et al, 2011). Next, pre-activated hCD34+ cells were plated in 48-well plates (2,5×$10^4$ cells/well in 100 µl of pre-activation medium). Transduction was completed by adding 100 µl of LV supernatants pre-incubated 15 min at 37° C. in absence or presence of peptides. 6 h post-transduction, all the conditions were diluted to 1 ml with differentiation medium (X-Vivo 20 with 50 U/ml penicillin, 50 mg/ml streptomycin and 2 mM L-glutamine (Gibco/Invitrogen), SCF (25 ng/ml), Flt-3 ligand (50 ng/ml), IL-6 (20 ng/ml) and IL-3 (10 ng/ml) (R&D Systems, Lille, France)). 2 days post-transduction, half of the cell suspension was replaced with fresh differentiation medium. The survival rates of discarded cells were evaluated by flow cytometry after labeling with 7-AAD. 5 to 6 days post-transduction, the transduction efficiency was evaluated by following the percentage of GFP expression in the cell population using flow cytometry. In the case of a lentiviral transduction protocol performed in presence of Retronectin, we used the dynamic preloading protocol of GALVTR-LVs onto retronectin coated plates (20 µg/cm²) as previously described (Jacome et al, 2009).

Production and Monitoring of HIS (BALB-Rag/γC) Mice

BALB/c rag2-/-γC-/- mice were housed under specific pathogen-free conditions at Genethon and treated in accordance with the guidelines of the animal ethical committee under protocol CE11003 (approval dates Mar. 1, 2011-Mar. 1, 2012). Briefly, transduced or untransduced hCD34+ cells ($10^5$ cells/mice) were injected intra-hepatically into irradiated BALB/c rag2-/- γC-/- newborn pups. Eleven to thirteen weeks post-injection, HIS (BALB-Rag/γC) mice were euthanized and effective engraftment level of human hematopoietic cells was monitored by flow cytometry in the blood, the thymus, the spleen and the bone marrow.

Cell Line Transfection with LAH4-L1 Derivatives 293T cells (1.5×10E5/well) were plated in 48-well plates the day before transfection. For transfection, 1 µg of pEGFP-C1 was mixed with the desired amount of peptide in 50 µl of 150 mM NaCl solution, vortexed and incubated 15 min at room temperature. Next, the DNA/peptide mix was diluted in 200 µl of DMEM without FCS and loaded onto cell monolayers. 3 hours post-transfection, the medium was replaced with DMEM containing 10% FCS. 48 h later, transfection efficiency was estimated by monitoring GFP expression using flow cytometry.

Results and Discussion

Effect of LAH4-L1 on Target Cell Transductions with Prototypic LVs Used in Gene Therapy.

To study the effect of LAH4-L1 on LV infectivity, HCT116 cells (or 293T cells for GP64-LVs) were transduced with GALVTR-LVs, RD114TR-LVs, MLV-A-LVs and VSV-G-LVs (FIG. 1A). As shown in FIG. 1B, LAH4-L1 promotes LV infectivity at different extent, with the highest effect observed for GALVTR-LVs. Interestingly, virus-like particles (VLPs), corresponding to LVs produced in the absence of any envelope glycoprotein construct, are unable to transduce target cells, even in the presence of LAH4-L1 (FIG. 1A). This result indicates that LAH4-L1 activity on LVs is dependent on the establishment of a receptor-mediated entry pathway into the cell.

Effect of LAH4-L1 on the Transduction of Human Hematopoietic Progenitors with GALVTR-LVs.

Figure 2:
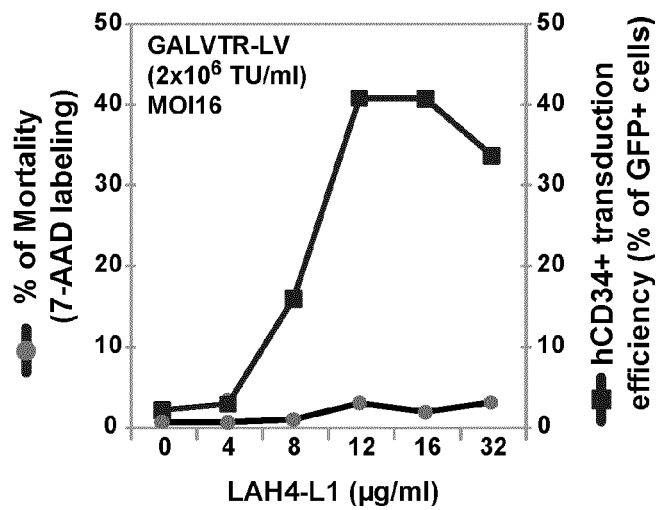
Figure 2:
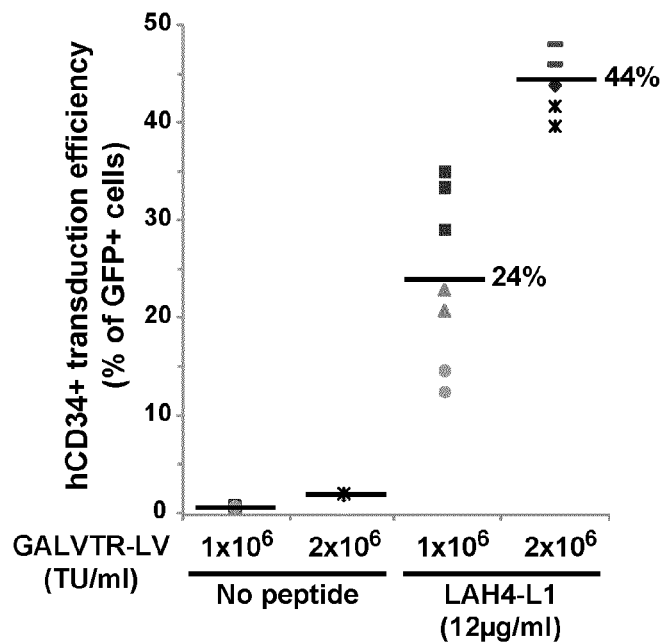

GALVTR-LVs are commonly used in gene therapy protocols designed to target human hematopoietic progenitors (Jacome et al, 2009). Hence, human CD34+ cells were obtained from umbilical cord blood (UCB) samples and were transduced with GALVTR-LVs in absence or presence of various concentrations of LAH4-L1. The optimal concentration of LAH4-L1 necessary to promote hCD34+ cells transduction was defined as 12 µg/ml (FIG. 2A), slightly higher than the one observed on HCT116 cells (FIG. 1A). We did not observe any cytotoxic effect of LAH4-L1 below 32 µg/ml (FIG. 2A). Furthermore, the transduction of hCD34+ cells in presence of LAH4-L1 is increasing proportionally to GALVTR-LV input and is reproducible from one UCB donor to another (FIG. 2B).

Monitoring of HIS (BALB-Rag/gC) Mice Engrafted with GALVTR-LV-Transduced-hCD34+ Cells: Safety Evaluation of the LAH4-L1 Peptide.

Figure 3:
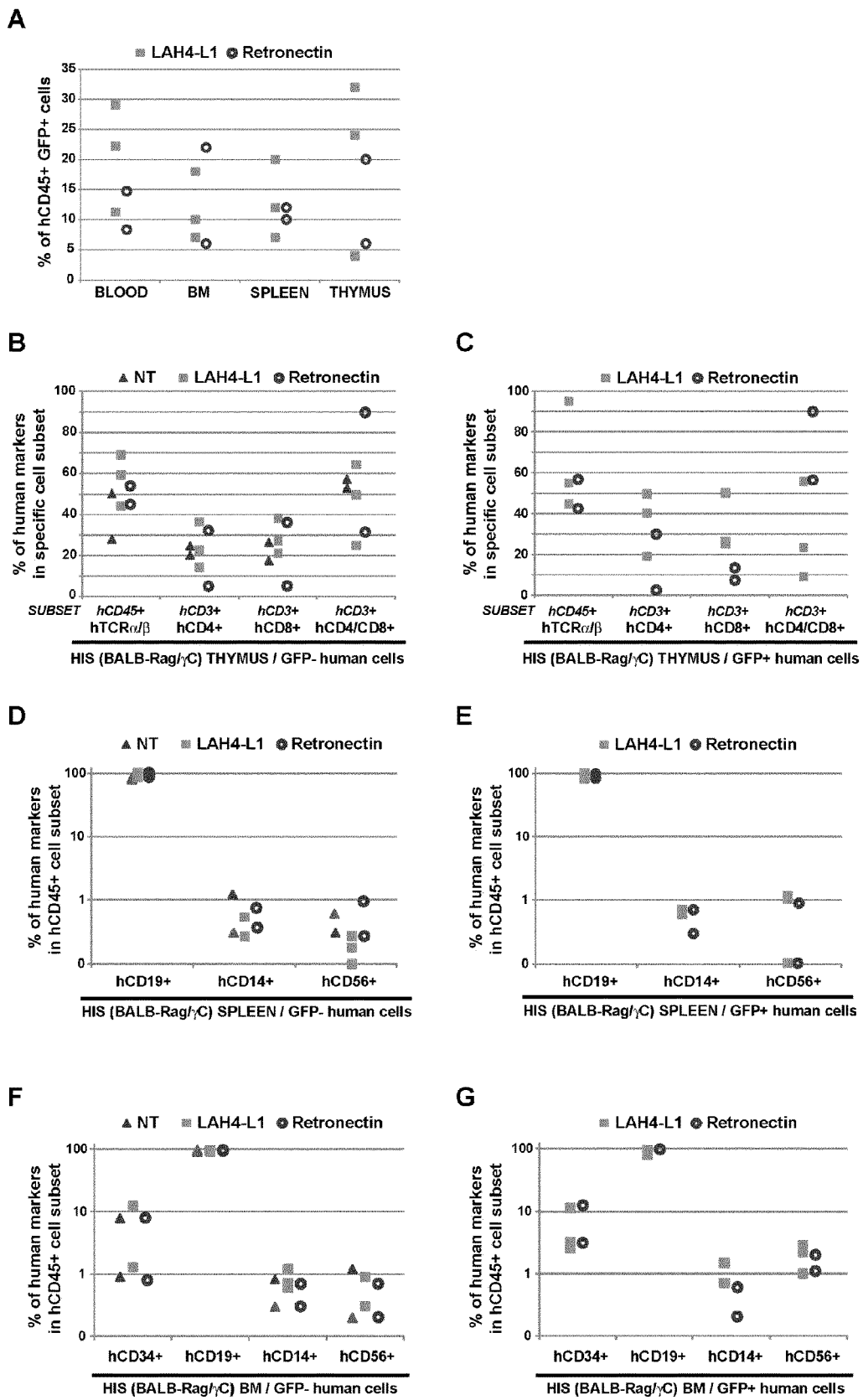

The use of newborn BALB/c rag2-/-γC-/- immunodeficient mice for injection of hCD34+ cells gives rise to robust human immune system reconstitution. The resulting animals are referred to as "Human Immune System" (HIS) (BALB-Rag/γC) mice (Legrand et al, 2008). This animal model is useful for the safety evaluation of compounds that have been in contact with human hematopoietic progenitors. Therefore, we decided to study the quality of human hematopoietic cells engraftment in the rag2−/−/γC−/− model for hCD34+ cells that have been transduced with GALVTR-LVs in presence of LAH4-L1 or Retronectin as a control. As shown in FIG. 3A, twelve weeks after injection in rag2−/−/ γC−/− mice, human CD45+ cells, transduced in presence of LAH4-L1 or Retronectin, are easily detectable in the blood, the bone marrow (BM), the spleen and the thymus. To exclude any cytotoxic or deleterious effect of LAH4-L1 on the total human cell population, the effective engraftment level was monitored in HIS (BALB-Rag/γC) mice for untransduced (FIG. 3B-D-F) and also transduced (FIG. 3C-E-G) human cells. As shown in FIGS. 3B and 3C, all the mice exhibited active human thymopoiesis in the thymus as evidenced by the percentages of human TCRα/β expression, human double-positive CD4/CD8 and single positive CD4 and CD8 human T cells (FIG. 3B-C). The spleen and the BM of the mice (FIG. 3D to 3G) contained a large population of human CD19+ cells indicating an active human B lymphoid development, as well as a population of human monocytes and natural killer cells. Human hematopoietic progenitors (hCD34+hCD45+ cells) are also detectable in the BM (FIG. 3F-G). Altogether, we did not observed any cytotoxic or deleterious effect of LAH4-L1 on the human immune system reconstitution in these mice. We observed a normal development of the different cell subsets of the human immune system, either in transduced or untransduced cells, arguing that LAH4-L1 is a safe and efficient culture additive.

Structure-Function Studies of LAH4-L1.

Figure 4:
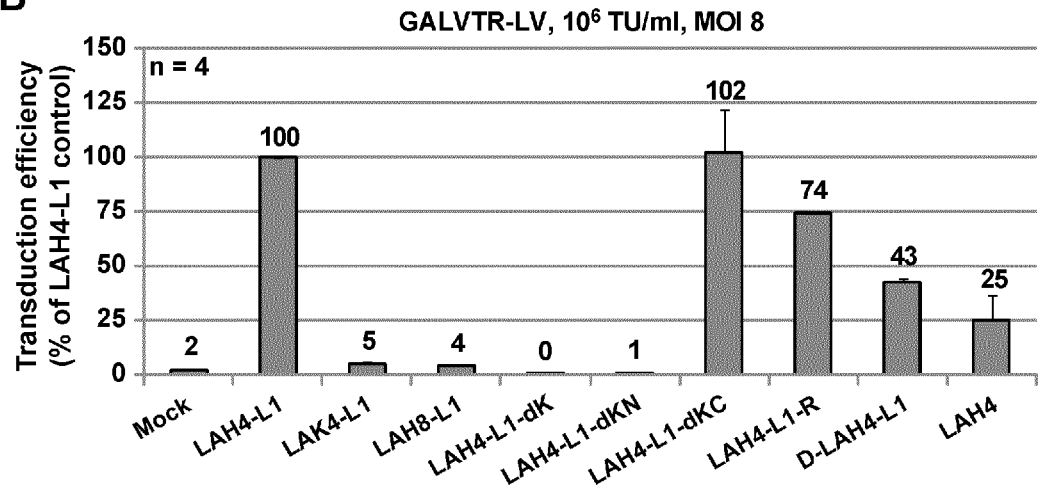
Figure 4:
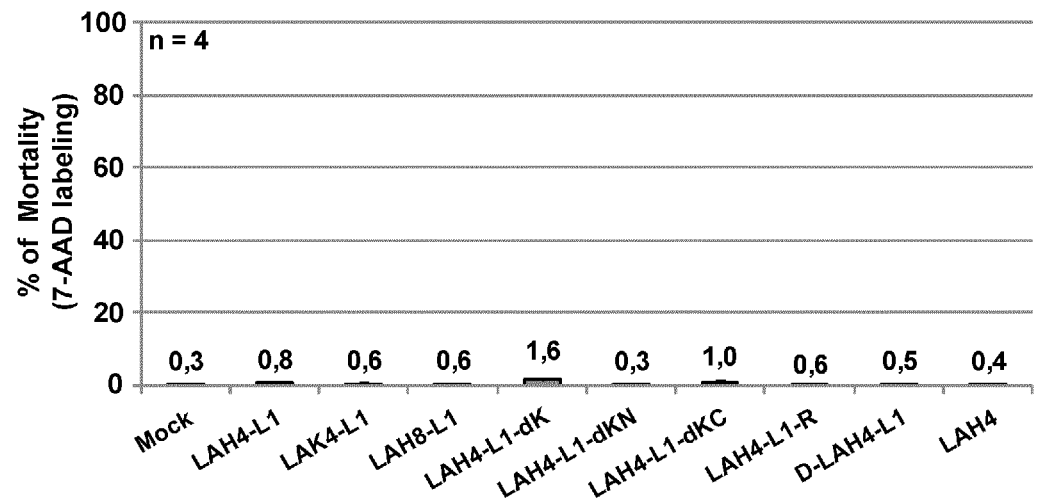

Derivatives of LAH4-L1 have been synthesized to better understand the specific role of Lysine and Histidine residues in the potentialization of LV infectivity (FIG. 4A). As shown in FIG. 4B, the replacement of the four Histidine residues with 4 lysine residues (LAK4-L1) is detrimental for the improvement of CD34+ cells transduction with GALVTR-LVs but is not the consequence of a strong cytotoxic effect (FIG. 4C). In our culture conditions at neutral pH, Histidine residues in LAH4-L1 are not protonated, allowing LAH4-L1 to adopt a transmembrane orientation. While in LAK4-L1, lysine residues lying along the entire peptide are protonated at neutral pH and certainly prevent this latter to adopt a transmembrane orientation. Moreover, LAK4-L 1 is inefficient despite the presence of nine cationic charges at neutral pH. This result strongly argues that LAH4-L1 is acting via a molecular mechanism that cannot be solely restricted to neutralization of repulsive charges on viral and cell membrane surface.

Next, we focused our attention on the two lysine residues present at both extremities of LAH4-L1. The replacement of the four lysine residues with four arginine residues (LAH4-L1-R) has no deleterious effect. LAH4-L 1-R is as efficient as LAH4-L1 to promote hCD34+ cells transduction with GALVTR-LVs (FIG. 4B), with no apparent cytotoxicity (FIG. 4C). On the contrary, the replacement of the four lysine residues with histidine residues (LAH8-L1) is detrimental. Therefore, the presence of cationic charges at neutral pH (lysine or arginine) seems necessary to enhance LV infectivity. To determine which of the lysine residues are crucial, either lying on the N-terminus or C-terminus extremity, three LAH4-L1 derivatives were designed (FIG. 4A): LAH4-L 1-dK (no lysine), LAH4-L1-dKN (deletion of the N-terminal lysine residues) and LAH4-L1-dKC (deletion of the C-terminal lysine residues). As shown in FIG. 4B, transduction of hCD34+ cells with GALVTR-LVs is not detectable in presence of LAH4-L 1-dK and LAH4-L1-dKN. The absence of lysine residues on the N-terminal extremity of LAH4-L1 is deleterious. On the contrary, LAH4-L1-dKC promotes hCD34+ cells transduction as efficiently as LAH4-L1.

To define whether D-amino acids can be used in place of L-amino acids, a LAH4-L1 peptide was synthesized with D-amino acids (D-LAH4-L1). As shown in FIG. 4B, D-LAH4-L1 still promotes lentiviral transduction but with a lower efficiency (43%) compared to LAH4-L1.

Design and Test of LAH4-L1 Isomers Harboring Leucine or Alanine Residues Between the Angle (60° to 180°) Subtended by the Histidine Residues in Schiffer-Edmundson's Wheel Representation.

Figure 5:
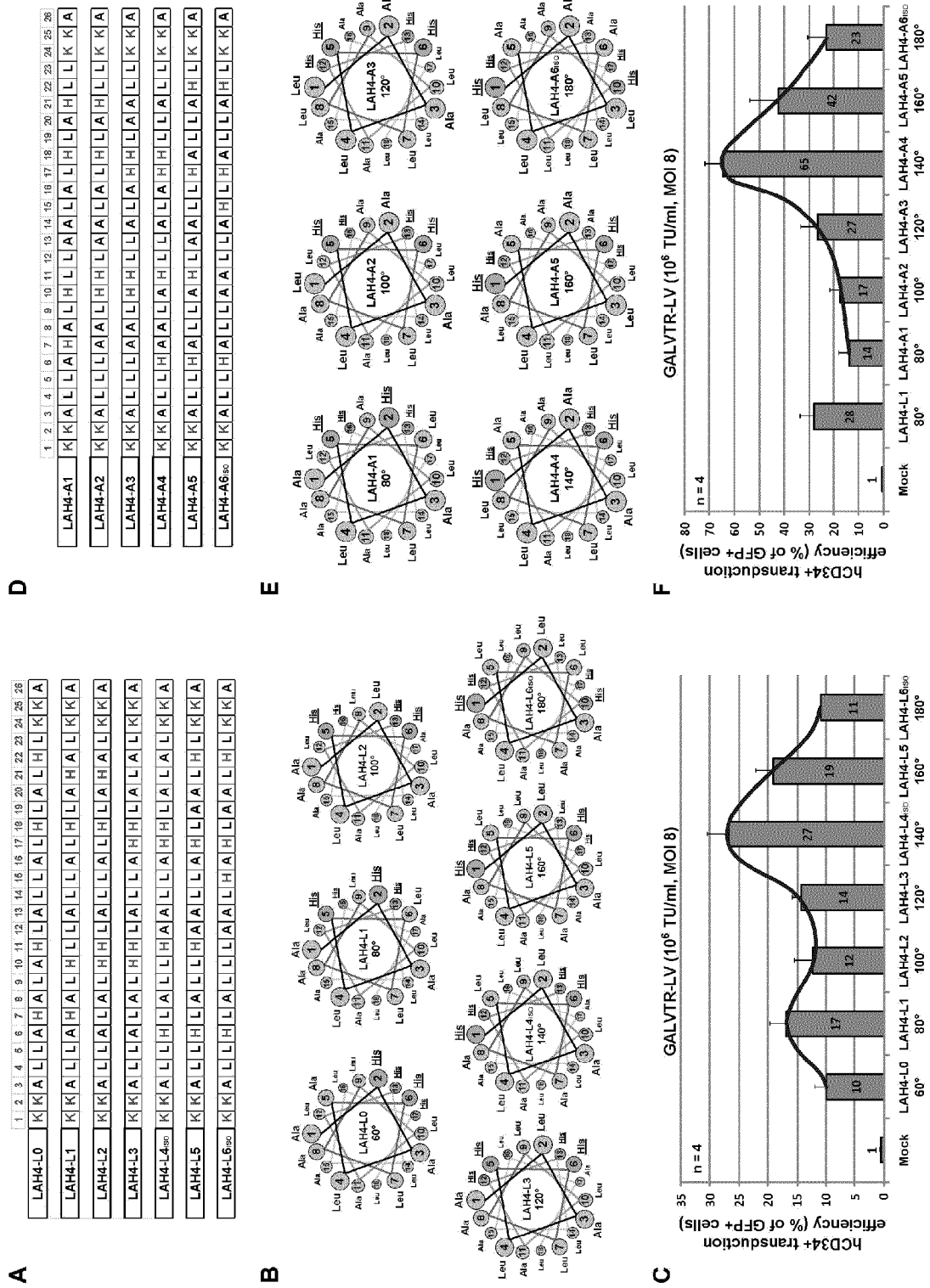

Peptide series of LAH4-L1 isomers have been prepared (FIGS. 5A and D). The first feature of these LAH4-L1 isomers is the difference in their angle subtended by the histidine residues (60 to 180°) when the peptide adopts a α-helical conformation at neutral pH (FIGS. 5B and E). The second feature is the choice of amino acid residues located between the two pairs of adjacent histidine residues when the peptide adopts a α-helical conformation. These residues either consist of Leucine residues for the L series (FIG. 5B) and alanine residues for the A series (FIG. 5E). Accordingly, peptide name nomenclature reflects the number of Alanine or leucine residues that are present between the two pairs of adjacent histidine residues in the Schiffer-Edmundson's wheel representation. For instance, peptide called LAH4-A4 is the peptide harboring four alanine residues between the two pairs of adjacent histidine residues leading to a hydrophilic angle of 140° (FIG. 5E). All these peptides have been tested for their capacity to promote the transduction of hCD34+ cells with GALVTR-LVs. Interestingly, in the L and A series, the most efficient peptides harbor an hydrophilic angle of 140°, namely LAH4-L4 and LAH4-A4. LAH4-A5, with a hydrophilic angle of 160°, is also highly efficient. These data have been confirmed with dose response curves (FIG. 6A). At 3 and LAH4-A4 is approximately four times more efficient than LAH4-L1 with no apparent cytotoxicity (FIG. 6B).

Structure-function Studies of LAH4-A4.

To study the role of the histidine residues, three LAH4-A4 derivatives were designed (FIG. 7A): LAH2-A4, harboring only two histidine residues, defining a hydrophilic angle of 100° in the Schiffer-Edmundson's wheel representation (FIG. 7B); LAH2-A6, harboring only two histidine residues, defining a hydrophilic angle of 140° (FIG. 7B) and K2-L10-A12-K2, an apolar helical peptide with lysine residues at each end of the helix. This peptide is corresponding to LAH4-A4 in which all the histidine residues have been replaced by alanine residues (FIG. 7A). As shown in FIG. 6C, LAH2-A6 promotes the transduction of hCD34+ cells with GALVTR-LV as efficiently as LAH4-A4 with no apparent cytotoxicity (FIG. 7D). On the contrary, LAH2-A4 is not functional. This peptide harbors a non optimal angle (100°) subtended by the two histidine residues in the Edmundson's wheel representation (FIG. 7B). Interestingly, the K2-L10A12-K2 peptide is promoting 17% of hCD34+ transduction level compared to LAH4-A4. Hence, histidine residues improve the efficiency of LAH4-A4 peptide but are not strictly necessary to promote lentiviral transduction.

To better define the role of the lysine residues, either lying on the N-terminus or C-terminus extremity of LAH4-A4, four LAH4-A4 derivatives were designed (FIG. 8A): LAH4-A4-dKN (deletion of the N-terminal lysine residues), LAH4-A4-K1N (deletion of only one N-terminal lysine residue), LAH4-A4-K3N (replacement of alanine at position 3 by a lysine) and LAH4-A4-dKC (deletion of the C-terminal lysine residues). In presence of LAH4-A4-dKN, transduction of hCD34+ cells with GALVTR-LVs is not detectable (FIG. 8B). This absence of transduction is not the consequence of a strong cytotoxic effect (FIG. 8C). The presence of only one lysine residue lying on the N-terminal extremity of LAH4-A4-K1N is sufficient to restore 60% of hCD34+ transduction level compared to LAH4-A4. Moreover, LAH4-A4 effect is not improved by the addition of an extra lysine on the N-terminal extremity. Indeed, LAH4-A4-K3N is as efficient as LAH4-A4 (FIG. 8B).

To define the minimal active sequence in LAH4-A4, shorter peptides were designed (FIG. 9A). As shown in FIG. 9B, the deletion of the C-terminal alanine (LAH4-A4-d1aa) slightly decreases the efficiency of LAH4-A4. Deletion of one amino acid residue on both side of the peptide (LAH4-A4-d2aa) decreases the efficiency to 30% compared to LAH4-A4. Finally, deletion of 2 amino acid residues on the C-terminal side (LAH4-A4-d2Caa) or 3 amino acid residues (LAH4-A4-d3aa) or 5 amino acids residues (LAH4-A4-d5aa) decreases the efficiency below 15% compared to LAH4-A4. In conclusion, a slight shortening of LAH4-A4 peptide length is detrimental for the promotion of lentiviral transduction of hCD34+ cells.

To determine whether the 4 alanine residues defining LAH4-A4 are the only 4 alanine residues necessary for LAH4-A4 potency, all the other alanine residues (position 3, 8, 16 and 26) lying in LAH4-A4 have been replaced with leucine residues (LAH4-A4-Leu). This peptide is still active but is two times less potent than LAH4-A4 (FIG. 9B).

Next, to determine whether the helical structure of LAH4 derivatives is crucial in the promotion of lentiviral transduction, a peptide harboring a proline in the middle of the helix (position 14) has been designed (LAH4-A4-P14). As shown in FIG. 9B, the insertion of the helix breaker proline abolishes 80% of the lentiviral transduction, suggesting a crucial role of the helix structure of LAH4-A4 in the promotion of lentiviral transduction.

Since all the LAH4 derivatives tested are amidated, a LAH4-A4 peptide with no amidation (LAH4-A4-dNH2) has been synthesized. As shown in FIG. 9B, amidated LAH4-A4 is approximately two times more efficient than in absence of amidation.

In 2007, a fragment of the human prostatic acid phosphatase (amino acid residues 240 to 290), identified as a strong enhancer of HIV-1 infectivity, was isolated from semen (Munch et al., 2007). This peptide called SEVI (human Semen Enhancer of Viral Infection) is able to promote the transduction of lentiviral vectors (Wurm et al., 2010). We tested the ability of SEVI and LAH4-A4 to promote the transduction of hCD34+ cells with GALVTR-LV. LAH4-A4 or SEVI peptides have been used at the same molarity of 2.2 µM. As shown in FIG. 10A, data obtained from three different cord blood donors indicate that the transduction in presence of LAH4-A4 is more efficient than in presence of SEVI, with no apparent cytotoxicity two days post-transduction (FIG. 10B).

LAH4 derivatives have been previously described as DNA transfection agents (Kichler et al, 2003). Therefore, we tested the capacity of LAH4-A4 to transfect 293T cells with a plasmid expressing the GFP protein. As shown in FIG. 11, 12µg/ml of LAH4-A4 are not sufficient to efficiently promote the transfection of 293T cells. However, an increase in LAH4-A4 concentration to 24 µg/ml allows highly efficient transfection of 293T cells, as observed for the LAH4-L1 control peptide. Interestingly, at the same concentration of 24 µg/ml, K2-L10A12-K2 is unable to promote cell transfection. The absence of histidine residues is detrimental for this activity, while at the same time, only 12 µg/ml of K2-L10A12-K2 is still able to promote some lentiviral transduction compared to LAH4-A4 (FIG. 7B).

Effect of LAH4-L1, LAH4-L4$_{ISO}$, LAH4-A4 and LAH4-A5 on the Transduction of Human Hematopoietic Progenitors with 114TR-LVs or GALV-MLV.

Hence, human CD34+ cells were obtained from umbilical cord blood (UCB) samples and were transduced with RD114TR-LV (3.8×10E6 TU/ml) or GALVTR-MLV (5×10E5 TU/ml) carrying a GFP reported gene, in absence or presence of 12 µg/ml of LAH4-L1 LAH4-L4$_{ISO}$, LAH4-A4 or LAH4-A5. We did not observe any cytotoxic effect of the peptides and all of them promoted entry of both viruses (FIG. 12). The LAH4-A4 peptide was the most efficient. The experiment with the GALVTR-MLV virus demonstrates that infection is improved even with a viral genome different from HIV.

REFERENCES

Bechinger B. 1996. Towards membrane protein design: pH-sensitive topology of histidine-containing polypeptides. J. Mol. Biol. 263: 768-75.

Charrier, S., M. Ferrand, M. Zerbato, G. Précigout, A. Viornery, S. Bucher-Laurent, S. Benkhelifa-Ziyyat, O. W. Merten, J. Perea, and A. Galy. 2011. Quantification of lentiviral vector copy numbers in individual hematopoietic colony-forming cells shows vector dose-dependent effects on the frequency and level of transduction. Gene Ther. 18:479-487.

Davis, H. E., M. Rosinski, J. R. Morgan, and M. L. Yarmush. 2004. Charged polymers modulate retrovirus transduction via membrane charge neutralization and virus aggregation. Biophys. J. 86:1234-42.

D'Costa, J., S. G. Mansfield, and L. M. Humeau. 2009. Lentiviral vectors in clinical trials: Current status. Curr. Opin. Mol. Ther. 11:554-64.

Follenzi, A., L. E. Ailles, S. Bakovic, M. Geuna, and L. Naldini. 2000. Gene transfer by lentiviral vectors is limited by nuclear translocation and rescued by HIV-1 pol sequences. Nat. Genet. 25: 217-222.

Georgescu J., V. H. O. Munhoz, and B. Bechinger. 2010. NMR structures of the histidine-rich peptide LAH4 in micellar environments: Membrane insertion, pH-dependent mode of antimicrobial action, and transfection. Biophys. J. 99:2507-15.

Jacome, A., S, Navarro, P. Río, R. M. Yañez, A. González-Murillo, M. L. Lozano, M. L. Lamana, J. Sevilla, T. Olive, C. Diaz-Heredia, I. Badell, J. Estella, L. Madero, G. Guenechea, J. Casado, J. C. Segovia, and J. A. Bueren. 2009. Lentiviral-mediated genetic correction of hematopoietic and mesenchymal progenitor cells from Fanconi anemia patients. Mol. Ther. 17:1083-92.

Kichler, A., C. Leborgne, J. März, O. Danos and B. Bechinger. 2003. Histidine-rich amphipathic peptide antibiotics promote efficient delivery of DNA into mammalian cells. Proc. Natl. Acad. Sci. USA. 100:1564-68.

Kutner, R. H., X. Y. Zhang and J. Reiser. 2009. Production, concentration and titration of pseudotyped HIV-1-based lentiviral vectors. Nat. Protoc. 4:495-505.

Kyte, J. and R. F. Doolittle. 1982. A simple method for displaying the hydropathic character of a protein. J. Mol. Biol. 157:105-132.

Legrand, N., K. Weijer, and H. Spits. 2008. Experimental model for the study of the human immune system: production and monitoring of "Human Immune System" Rag2-/- gamma C-/- mice. Methods Mol. Biol. 415:65-82.

Mason, A. J., W. Moussaoui, T. Abdelrahman, A. Boukhari, P. Bertani, A. Marquette, P. Shooshtarizaheh, G. Moulay, N. Boehm, B. Guerold, R. J. Sawers, A. Kichler, M. H. Metz-Boutique, E. Candolfi, G. Prévost, and B. Bechinger. 2009. Structural determinants of antimicrobial and antiplasmodial activity and selectivity in histidine-rich amphipathic cationic peptides. J. Biol. Chem. 284: 119-33.

Merten, O. W., S. Charrier, N. Laroudie, S. Fauchille, C. Dugué, C. Jenny, M. Audit, M. A. Zanta-Boussif, H. Chautard, M. Radrizzani, G. Vallanti, L. Naldini, P. Noguiez-Hellin, and A. Galy. 2011. Large-scale manufacture and characterization of a lentiviral vector produced for clinical ex vivo gene therapy application. Hum. Gene Ther. 22:343-56.

Merten, O. W. 2004. State-of-the-art of the production of retroviral vectors. *J. Gene Med.* 6 Suppl 1, S105-124.

Munch, J., E. Rucker, L. Standker, K. Adermann, C. Goffinet, M. Schindler, S. Wildum, R. Chinnadurai, D. Rajan, A. Specht, G. Gimenez-Gallego, P. C. Sanchez, D. M. Fowler, A. Koulov, J. W. Kelly, W. Mothes, J. C. Grivel, L. Margolis, O. T. Keppler, W. G. Forssmann, and F. Kirchhoff. 2007. Semen-derived amyloid fibrils drastically enhance HIV infection. Cell 131:1059-71.

Naldini, L., U. Blömer, P. Gallay, D. Ory, R. Mulligan, F. H. Gage, I. M. Verma, and D. Trono. 1996. In vivo gene delivery and stable transduction of nondividing cells by a lentiviral vector. Science. 272: 263-7.

Novelli, E M., L. Cheng, Y. Yang, W. Leung, M. Ramirez, V. Tanavde, C. Enger, and C. I. Civin. 1999. Ex vivo culture of cord blood CD34+ cells expands progenitor cell numbers, preserves engraftment capacity in nonobese diabetic/severe combined immunodeficient mice, and enhances retroviral transduction efficiency. Hum. Gene Ther. 10:2927-40.

Pollok, K. E., and D. A. Williams. 1999. Facilitation of retrovirus-mediated gene transfer into hematopoietic stem and progenitor cells and peripheral blood T-lymphocytes utilizing recombinant fibronectin fragments. Curr. Opin. Mol. Ther. 1:595-604.

Roan, N. R., J. Munch, N. Arhel, W. Mothes, J. Neidleman, A. Kobayashi, K. Smith-McCune, F. Kirchhoff, and W. C. Greene. 2009. The cationic properties of SEVI underlie its ability to enhance human immunodeficiency virus infection. J. Virol. 83:73-80.

Rodrigues, T., M. J. Carrondo, P. M. Alves, and P. E. Cruz. 2007. Purification of retroviral vectors for clinical application: biological implications and technological challenges. J. Biotechnol. 127:520-41.

Sandrin, V., B. Boson, P. Salmon, W. Gay, D. Negre, R. Le Grand, D. Trono, and F. L. Cosset. 2002. Lentiviral vectors pseudotyped with a modified RD114 envelope glycoprotein show increased stability in sera and augmented transduction of primary lymphocytes and CD34+ cells derived from human and nonhuman primates. Blood 100:823-32.

Schiffer, M. and A. B. Edmundson. 1967. Use of helical wheels to represent the structures of proteins and to identify segments with helical potential. Biophys. J. 7: 121-35.

Wurm, M., A. Schambach, D. Lindemann, H. Hanenberg, L. Standker, W. Forssmann, R. Blasczyk and P. A. Horn. 2010. The influence of semen-derived enhancer of virus infection on the efficiency of retroviral gene transfer. J. Gen. Med. 12:137-46.

---

The invention claimed is:

1. A method for promoting the infection of an eukaryotic cell by a virus or a viral particle, comprising contacting a cell or a subject in need thereof with the virus or viral particle and with a peptide having the sequence of SEQ ID NO: 14.

2. An isolated peptide selected in the group consisting of SEQ ID NOs: 8-27.

3. A method for infecting eukaryotic cells with a virus or a viral particle or for increasing the efficiency of a nucleic acid transfer into a target cell with a viral particle, comprising contacting the cells with the virus or viral particle in the presence of a peptide having the sequence of SEQ ID NO: 14.

4. A method for increasing the efficiency of a nucleic acid transfer into a target cell with a viral particle, comprising contacting the target cell with the viral particle in the presence of a peptide having the sequence of SEQ ID NO: 14 to improve the transduction efficiency of a virus or viral particle to promote transfer of a nucleic acid into the target cell.

5. A method for diagnosing an infection by a virus in a subject, comprising incubating a sample of the subject with an eukaryotic cell and a peptide having the sequence of SEQ ID NO: 14, in order to amplify any virus contained in said sample, and identifying the amplified virus.

6. A method for gene therapy, comprising administering to a subject in need thereof a virus or viral particle comprising a therapeutic gene, and administering to the subject a peptide having the sequence of SEQ ID NO: 14 for promoting the infection of an eukaryotic cell by a virus or a viral particle.

7. The method according to claim 1, wherein the virus or viral particle is an enveloped virus or viral particle.

8. The method according to claim 3, wherein the cells are hematopoietic progenitor/stem cells.

9. The method according to claim 4, wherein the cells are hematopoietic progenitor/stem cells.

10. The method according to claim 1, wherein said sequence is amidated at the C-terminus thereof.

11. The method according to claim 1, wherein the cell is a hematopoietic progenitor or stem cell.

12. The method according to claim 3, wherein said sequence is amidated at the C-terminus thereof.

13. The method according to claim 4, wherein said sequence is amidated at the C-terminus thereof.

14. The method according to claim 5, wherein said sequence is amidated at the C-terminus thereof.

15. The method according to claim 6, wherein said sequence is amidated at the C-terminus thereof.

* * * * *

SEQUENCE LISTING

```
<160> NUMBER OF SEQ ID NOS: 37

<210> SEQ ID NO 1
<211> LENGTH: 26
<212> TYPE: PRT
<213> ORGANISM: artificial
<220> FEATURE:
<223> OTHER INFORMATION: LAH4

<400> SEQUENCE: 1

Lys Lys Ala Leu Leu Ala Leu Ala Leu His His Leu Ala His Leu Ala
1               5                   10                  15

Leu His Leu Ala Leu Ala Leu Lys Lys Ala
            20                  25

<210> SEQ ID NO 2
<211> LENGTH: 26
<212> TYPE: PRT
<213> ORGANISM: artificial
<220> FEATURE:
<223> OTHER INFORMATION: LAH4-L1 (all L- or all D-amino acids)

<400> SEQUENCE: 2

Lys Lys Ala Leu Leu Ala His Ala Leu His Leu Leu Ala Leu Leu Ala
1               5                   10                  15

Leu His Leu Ala His Ala Leu Lys Lys Ala
            20                  25

<210> SEQ ID NO 3
<211> LENGTH: 24
<212> TYPE: PRT
<213> ORGANISM: artificial
```

```
<220> FEATURE:
<223> OTHER INFORMATION: LAH4-L1-dKC

<400> SEQUENCE: 3

Lys Lys Ala Leu Leu Ala His Ala Leu His Leu Leu Ala Leu Leu Ala
1               5                   10                  15

Leu His Leu Ala His Ala Leu Ala
            20

<210> SEQ ID NO 4
<211> LENGTH: 26
<212> TYPE: PRT
<213> ORGANISM: artificial
<220> FEATURE:
<223> OTHER INFORMATION: LAH4-L1-R

<400> SEQUENCE: 4

Arg Arg Ala Leu Leu Ala His Ala Leu His Leu Leu Ala Leu Leu Ala
1               5                   10                  15

Leu His Leu Ala His Ala Leu Arg Arg Ala
            20                  25

<210> SEQ ID NO 5
<211> LENGTH: 26
<212> TYPE: PRT
<213> ORGANISM: artificial
<220> FEATURE:
<223> OTHER INFORMATION: LAH4-L0

<400> SEQUENCE: 5

Lys Lys Ala Leu Leu Ala His Ala Leu Ala His Leu Ala Leu Leu Ala
1               5                   10                  15

Leu His Leu Ala Leu His Leu Lys Lys Ala
            20                  25

<210> SEQ ID NO 6
<211> LENGTH: 26
<212> TYPE: PRT
<213> ORGANISM: artificial
<220> FEATURE:
<223> OTHER INFORMATION: LAH4-L2

<400> SEQUENCE: 6

Lys Lys Ala Leu Leu Ala Leu Ala Leu His His Leu Ala Leu Leu Ala
1               5                   10                  15

Leu His Leu Ala His Ala Leu Lys Lys Ala
            20                  25

<210> SEQ ID NO 7
<211> LENGTH: 26
<212> TYPE: PRT
<213> ORGANISM: artificial
<220> FEATURE:
<223> OTHER INFORMATION: LAH4-L3

<400> SEQUENCE: 7

Lys Lys Ala Leu Leu Ala Leu Ala Leu His His Leu Ala Leu Leu Ala
1               5                   10                  15

His His Leu Ala Leu Ala Leu Lys Lys Ala
            20                  25
```

```
<210> SEQ ID NO 8
<211> LENGTH: 26
<212> TYPE: PRT
<213> ORGANISM: artificial
<220> FEATURE:
<223> OTHER INFORMATION: LAH4-L4iso

<400> SEQUENCE: 8

Lys Lys Ala Leu Leu His Leu Ala Leu Leu His Ala Ala Leu Leu Ala
1               5                   10                  15

His His Leu Ala Leu Ala Leu Lys Lys Ala
            20                  25

<210> SEQ ID NO 9
<211> LENGTH: 26
<212> TYPE: PRT
<213> ORGANISM: artificial
<220> FEATURE:
<223> OTHER INFORMATION: LAH4-L5

<400> SEQUENCE: 9

Lys Lys Ala Leu Leu His Leu Ala Leu Leu His Ala Ala Leu Leu Ala
1               5                   10                  15

His Leu Ala Ala Leu His Leu Lys Lys Ala
            20                  25

<210> SEQ ID NO 10
<211> LENGTH: 26
<212> TYPE: PRT
<213> ORGANISM: artificial
<220> FEATURE:
<223> OTHER INFORMATION: LAH4-L6iso

<400> SEQUENCE: 10

Lys Lys Ala Leu Leu His Leu Ala Leu Leu Leu Ala Ala Leu His Ala
1               5                   10                  15

His Leu Ala Ala Leu His Leu Lys Lys Ala
            20                  25

<210> SEQ ID NO 11
<211> LENGTH: 26
<212> TYPE: PRT
<213> ORGANISM: artificial
<220> FEATURE:
<223> OTHER INFORMATION: LAH4-A1

<400> SEQUENCE: 11

Lys Lys Ala Leu Leu Ala His Ala Leu His Leu Leu Ala Ala Leu Ala
1               5                   10                  15

Leu His Leu Ala His Leu Leu Lys Lys Ala
            20                  25

<210> SEQ ID NO 12
<211> LENGTH: 26
<212> TYPE: PRT
<213> ORGANISM: artificial
<220> FEATURE:
<223> OTHER INFORMATION: LAH4-A2

<400> SEQUENCE: 12

Lys Lys Ala Leu Leu Leu Ala Ala Leu His His Leu Ala Ala Leu Ala
1               5                   10                  15

Leu His Leu Ala His Leu Leu Lys Lys Ala
            20                  25
```

```
<210> SEQ ID NO 13
<211> LENGTH: 26
<212> TYPE: PRT
<213> ORGANISM: artificial
<220> FEATURE:
<223> OTHER INFORMATION: LAH4-A3

<400> SEQUENCE: 13

Lys Lys Ala Leu Leu Ala Ala Leu His His Leu Leu Ala Leu Ala
1               5                   10                  15

His His Leu Ala Ala Leu Leu Lys Lys Ala
            20                  25

<210> SEQ ID NO 14
<211> LENGTH: 26
<212> TYPE: PRT
<213> ORGANISM: artificial
<220> FEATURE:
<223> OTHER INFORMATION: LAH4-A4

<400> SEQUENCE: 14

Lys Lys Ala Leu Leu His Ala Ala Leu Ala His Leu Leu Ala Leu Ala
1               5                   10                  15

His His Leu Leu Ala Leu Leu Lys Lys Ala
            20                  25

<210> SEQ ID NO 15
<211> LENGTH: 26
<212> TYPE: PRT
<213> ORGANISM: artificial
<220> FEATURE:
<223> OTHER INFORMATION: LAH4-A5

<400> SEQUENCE: 15

Lys Lys Ala Leu Leu His Ala Leu Leu Ala His Leu Ala Ala Leu Leu
1               5                   10                  15

His Ala Leu Leu Ala His Leu Lys Lys Ala
            20                  25

<210> SEQ ID NO 16
<211> LENGTH: 26
<212> TYPE: PRT
<213> ORGANISM: artificial
<220> FEATURE:
<223> OTHER INFORMATION: LAH4-A6iso

<400> SEQUENCE: 16

Lys Lys Ala Leu Leu His Ala Leu Leu Ala Ala Leu Leu Ala His Leu
1               5                   10                  15

His Ala Leu Leu Ala His Leu Lys Lys Ala
            20                  25

<210> SEQ ID NO 17
<211> LENGTH: 25
<212> TYPE: PRT
<213> ORGANISM: artificial
<220> FEATURE:
<223> OTHER INFORMATION: LAH4-A4-K1N

<400> SEQUENCE: 17

Lys Ala Leu Leu His Ala Ala Leu Ala His Leu Leu Ala Leu Ala His
1               5                   10                  15

His Leu Leu Ala Leu Leu Lys Lys Ala
            20                  25
```

```
<210> SEQ ID NO 18
<211> LENGTH: 26
<212> TYPE: PRT
<213> ORGANISM: artificial
<220> FEATURE:
<223> OTHER INFORMATION: LAH4-A4-K3N

<400> SEQUENCE: 18

Lys Lys Lys Leu Leu His Ala Ala Leu Ala His Leu Leu Ala Leu Ala
1               5                   10                  15

His His Leu Leu Ala Leu Leu Lys Lys Ala
            20                  25

<210> SEQ ID NO 19
<211> LENGTH: 24
<212> TYPE: PRT
<213> ORGANISM: artificial
<220> FEATURE:
<223> OTHER INFORMATION: LAH4-A4-dKC

<400> SEQUENCE: 19

Lys Lys Ala Leu Leu His Ala Ala Leu Ala His Leu Leu Ala Leu Ala
1               5                   10                  15

His His Leu Leu Ala Leu Leu Ala
            20

<210> SEQ ID NO 20
<211> LENGTH: 25
<212> TYPE: PRT
<213> ORGANISM: artificial
<220> FEATURE:
<223> OTHER INFORMATION: LAH4-A4-d1aa

<400> SEQUENCE: 20

Lys Lys Ala Leu Leu His Ala Ala Leu Ala His Leu Leu Ala Leu Ala
1               5                   10                  15

His His Leu Leu Ala Leu Leu Lys Lys
            20                  25

<210> SEQ ID NO 21
<211> LENGTH: 24
<212> TYPE: PRT
<213> ORGANISM: artificial
<220> FEATURE:
<223> OTHER INFORMATION: LAH4-A4-d2aa

<400> SEQUENCE: 21

Lys Lys Leu Leu His Ala Ala Leu Ala His Leu Leu Ala Leu Ala His
1               5                   10                  15

His Leu Leu Ala Leu Leu Lys Lys
            20

<210> SEQ ID NO 22
<211> LENGTH: 24
<212> TYPE: PRT
<213> ORGANISM: artificial
<220> FEATURE:
<223> OTHER INFORMATION: LAH4-A4-d2Caa

<400> SEQUENCE: 22

Lys Lys Ala Leu Leu His Ala Ala Leu Ala His Leu Leu Ala Leu Ala
1               5                   10                  15

His His Leu Leu Ala Leu Lys Lys
            20
```

```
<210> SEQ ID NO 23
<211> LENGTH: 23
<212> TYPE: PRT
<213> ORGANISM: artificial
<220> FEATURE:
<223> OTHER INFORMATION: LAH4-A4-d3aa

<400> SEQUENCE: 23

Lys Lys Leu His Ala Ala Leu Ala His Leu Leu Ala Leu Ala His His
1               5                   10                  15

Leu Leu Ala Leu Leu Lys Lys
            20

<210> SEQ ID NO 24
<211> LENGTH: 21
<212> TYPE: PRT
<213> ORGANISM: artificial
<220> FEATURE:
<223> OTHER INFORMATION: LAH4-A4-d5aa

<400> SEQUENCE: 24

Lys Lys Leu His Ala Ala Leu Ala His Leu Leu Ala Leu Ala His His
1               5                   10                  15

Leu Leu Ala Lys Lys
            20

<210> SEQ ID NO 25
<211> LENGTH: 26
<212> TYPE: PRT
<213> ORGANISM: artificial
<220> FEATURE:
<223> OTHER INFORMATION: LAH2-A6

<400> SEQUENCE: 25

Lys Lys Ala Leu Leu His Ala Ala Leu Ala His Leu Leu Ala Leu Ala
1               5                   10                  15

Ala Ala Leu Leu Ala Leu Leu Lys Lys Ala
            20                  25

<210> SEQ ID NO 26
<211> LENGTH: 26
<212> TYPE: PRT
<213> ORGANISM: artificial
<220> FEATURE:
<223> OTHER INFORMATION: K2-L10A12-K2

<400> SEQUENCE: 26

Lys Lys Ala Leu Leu Ala Ala Ala Leu Ala Ala Leu Leu Ala Leu Ala
1               5                   10                  15

Ala Ala Leu Leu Ala Leu Leu Lys Lys Ala
            20                  25

<210> SEQ ID NO 27
<211> LENGTH: 26
<212> TYPE: PRT
<213> ORGANISM: artificial
<220> FEATURE:
<223> OTHER INFORMATION: LAH4-A4-Leu

<400> SEQUENCE: 27

Lys Lys Leu Leu Leu His Ala Leu Leu Ala His Leu Leu Ala Leu Leu
1               5                   10                  15

His His Leu Leu Ala Leu Leu Lys Lys Leu
            20                  25
```

<210> SEQ ID NO 28
<211> LENGTH: 26
<212> TYPE: PRT
<213> ORGANISM: artificial
<220> FEATURE:
<223> OTHER INFORMATION: LAH4-A4-P14

<400> SEQUENCE: 28

Lys Lys Ala Leu Leu His Ala Ala Leu Ala His Leu Leu Pro Leu Ala
1               5                   10                  15

His His Leu Leu Ala Leu Leu Lys Lys Ala
            20                  25

<210> SEQ ID NO 29
<211> LENGTH: 26
<212> TYPE: PRT
<213> ORGANISM: artificial
<220> FEATURE:
<223> OTHER INFORMATION: LAK4-L1

<400> SEQUENCE: 29

Lys Lys Ala Leu Leu Ala Lys Ala Leu Lys Leu Leu Ala Leu Leu Ala
1               5                   10                  15

Leu Lys Leu Ala Lys Ala Leu Lys Lys Ala
            20                  25

<210> SEQ ID NO 30
<211> LENGTH: 26
<212> TYPE: PRT
<213> ORGANISM: artificial
<220> FEATURE:
<223> OTHER INFORMATION: LAH8-L1

<400> SEQUENCE: 30

His His Ala Leu Leu Ala His Ala Leu His Leu Leu Ala Leu Leu Ala
1               5                   10                  15

Leu His Leu Ala His Ala Leu His His Ala
            20                  25

<210> SEQ ID NO 31
<211> LENGTH: 22
<212> TYPE: PRT
<213> ORGANISM: artificial
<220> FEATURE:
<223> OTHER INFORMATION: LAH4-L1-dK

<400> SEQUENCE: 31

Ala Leu Leu Ala His Ala Leu His Leu Leu Ala Leu Leu Ala Leu His
1               5                   10                  15

Leu Ala His Ala Leu Ala
            20

<210> SEQ ID NO 32
<211> LENGTH: 24
<212> TYPE: PRT
<213> ORGANISM: artificial
<220> FEATURE:
<223> OTHER INFORMATION: LAH4-L1-dKN

<400> SEQUENCE: 32

Ala Leu Leu Ala His Ala Leu His Leu Ala Leu Leu Ala Leu His
1               5                   10                  15

Leu Ala His Ala Leu Lys Lys Ala
            20

```
<210> SEQ ID NO 33
<211> LENGTH: 24
<212> TYPE: PRT
<213> ORGANISM: artificial
<220> FEATURE:
<223> OTHER INFORMATION: LAH4-A4-dKN

<400> SEQUENCE: 33

Ala Leu Leu His Ala Ala Leu Ala His Leu Leu Ala Leu Ala His His
1               5                   10                  15

Leu Leu Ala Leu Leu Lys Lys Ala
            20

<210> SEQ ID NO 34
<211> LENGTH: 26
<212> TYPE: PRT
<213> ORGANISM: artificial
<220> FEATURE:
<223> OTHER INFORMATION: LAH2-A4

<400> SEQUENCE: 34

Lys Lys Ala Leu Leu Ala Ala Ala Leu Ala Ala Leu Leu Ala Leu Ala
1               5                   10                  15

His His Leu Leu Ala Leu Leu Lys Lys Ala
            20                  25

<210> SEQ ID NO 35
<211> LENGTH: 39
<212> TYPE: PRT
<213> ORGANISM: artificial
<220> FEATURE:
<223> OTHER INFORMATION: SEVI

<400> SEQUENCE: 35

Gly Ile His Lys Gln Lys Glu Lys Ser Arg Leu Gln Gly Gly Val Leu
1               5                   10                  15

Val Asn Glu Ile Leu Asn His Met Lys Arg Ala Thr Gln Ile Pro Ser
            20                  25                  30

Tyr Lys Lys Leu Ile Met Tyr
        35

<210> SEQ ID NO 36
<211> LENGTH: 26
<212> TYPE: PRT
<213> ORGANISM: artificial
<220> FEATURE:
<223> OTHER INFORMATION: LAH4-L4

<400> SEQUENCE: 36

Lys Lys Ala Leu Leu Ala Leu Ala Leu His His Leu Ala Leu Leu Ala
1               5                   10                  15

His Leu Leu Ala Leu His Leu Lys Lys Ala
            20                  25

<210> SEQ ID NO 37
<211> LENGTH: 27
<212> TYPE: PRT
<213> ORGANISM: artificial
<220> FEATURE:
<223> OTHER INFORMATION: LAH4-L6
```

```
<400> SEQUENCE: 37

Lys Lys Lys Lys Ala Leu Leu His Leu His Leu Leu Ala Leu His Leu
1               5                   10                  15
His Leu Leu Ala Leu Leu Ala Leu Lys Lys Lys
                20              25
```